(12) United States Patent
Hinestroza et al.

(10) Patent No.: US 11,478,774 B2
(45) Date of Patent: Oct. 25, 2022

(54) METAL ORGANIC FRAMEWORKS AND METHODS OF MAKING AND USING SAME

(71) Applicant: Cornell University, Ithaca, NY (US)

(72) Inventors: Juan Paulo Hinestroza, Ithaca, NY (US); Manuela Leticia Kim, Buenos Aires (AR); Eugenio Hernan Otal, Buenos Aires (AR)

(73) Assignee: CORNELL UNIVERSITY, Ithaca, NY (US)

(*) Notice: Subject to any disclaimer, the term of this patent is extended or adjusted under 35 U.S.C. 154(b) by 900 days.

(21) Appl. No.: 16/329,561

(22) PCT Filed: Aug. 29, 2017

(86) PCT No.: PCT/US2017/049097
§ 371 (c)(1),
(2) Date: Feb. 28, 2019

(87) PCT Pub. No.: WO2018/044874
PCT Pub. Date: Mar. 8, 2018

(65) Prior Publication Data
US 2019/0217270 A1 Jul. 18, 2019

Related U.S. Application Data

(60) Provisional application No. 62/380,646, filed on Aug. 29, 2016.

(51) Int. Cl.
*C07F 5/06* (2006.01)
*B01J 31/16* (2006.01)
(Continued)

(52) U.S. Cl.
CPC ............ *B01J 20/226* (2013.01); *B01D 53/04* (2013.01); *B01J 20/28016* (2013.01);
(Continued)

(58) Field of Classification Search
CPC ....... C07C 51/412; C07C 57/15; C07C 63/24; C07C 63/307; C07C 7/20; C07F 1/005;
(Continued)

(56) References Cited

U.S. PATENT DOCUMENTS 8,227,375 B2   7/2012   Willis et al.
8,466,285 B2   6/2013   James et al.
(Continued)

FOREIGN PATENT DOCUMENTS

CN   103432997 A   12/2013
CN   104138746     11/2014
(Continued)

OTHER PUBLICATIONS

Lanchas et al., Towards multicomponent MOFs via solvent-free synthesis under conventional oven and microwave assisted heating, Inorganic Chemistry Frontiers, Feb. 11, 2015, No. 2, pp. 425-433.
(Continued)

*Primary Examiner* — Frank M Lawrence, Jr.
(74) *Attorney, Agent, or Firm* — Paul J. Roman, Jr.; Johnson, Marcou, Isaacs & Nix LLC

(57) ABSTRACT

Metal Organic Framework (MOF) materials and methods of making MOF materials. The methods include grinding of mixtures of metal hydroxide(s) and ligand(s). The MOF materials may have at least two different ligands. The MOF materials may have open metal sites. The MOF materials can be used in gas storage applications.

27 Claims, 16 Drawing Sheets a

(51) Int. Cl.
- *B01J 20/22* (2006.01)
- *B01J 31/22* (2006.01)
- *C07C 51/41* (2006.01)
- *C07F 1/00* (2006.01)
- *B01D 53/04* (2006.01)
- *B01J 20/28* (2006.01)
- *B01J 20/30* (2006.01)
- *C07C 7/20* (2006.01)
- *C10L 3/06* (2006.01)
- *F17C 11/00* (2006.01)

(52) U.S. Cl.
CPC ... *B01J 20/28083* (2013.01); *B01J 20/28085* (2013.01); *B01J 20/3007* (2013.01); *B01J 20/3021* (2013.01); *B01J 20/3085* (2013.01); *B01J 31/16* (2013.01); *B01J 31/22* (2013.01); *C07C 7/20* (2013.01); *C07C 51/412* (2013.01); *C07F 1/005* (2013.01); *C07F 5/069* (2013.01); *C10L 3/06* (2013.01); *F17C 11/007* (2013.01); *B01D 2253/204* (2013.01); *B01D 2257/7025* (2013.01); *C10L 2230/14* (2013.01); *C10L 2290/542* (2013.01)

(58) Field of Classification Search
CPC ........ C07F 5/069; F17C 11/007; B01D 53/04; B01D 2253/204; B01D 2257/7025; C10L 2230/14; C10L 2290/542; C10L 3/06; B01J 20/226; B01J 20/28016; B01J 20/28083; B01J 20/28085; B01J 20/3007; B01J 20/3021; B01J 20/3085; B01J 31/16; B01J 31/20; Y02C 20/20
USPC ............... 96/108; 95/90, 900, 902; 502/401; 206/0.7
See application file for complete search history.

(56) References Cited

U.S. PATENT DOCUMENTS

| | | | |
|---|---|---|---|
| 9,777,029 B2* | 10/2017 | Mora Vallejo | C07F 11/005 |
| 9,884,307 B2* | 2/2018 | Matoga | C07C 63/307 |
| 2009/0143595 A1* | 6/2009 | James | C07C 51/418 560/96 |
| 2014/0194639 A1 | 7/2014 | Chen et al. | |
| 2015/0031908 A1 | 1/2015 | Bury et al. | |
| 2015/0266885 A1* | 9/2015 | Banerjee | C07D 487/22 540/472 |
| 2016/0176070 A1 | 6/2016 | James et al. | |
| 2016/0185806 A1* | 6/2016 | Mora Vallejo | C07F 11/005 556/61 |
| 2018/0147284 A1* | 5/2018 | Orellana-Tavra | A61K 31/713 |

FOREIGN PATENT DOCUMENTS

| | | |
|---|---|---|
| CN | 105061512 A | 11/2015 |
| CN | 106674537 A | 5/2017 |
| CN | 106957439 A | 7/2017 |
| KR | 20150068748 A | 6/2015 |
| WO | 2013/058845 A1 | 4/2013 |
| WO | 2013/160683 A1 | 10/2013 |
| WO | WO 2014/054955 A1 * | 4/2014 |
| WO | 2017/089410 A1 | 6/2017 |
| WO | 2017/117410 A | 7/2017 |

OTHER PUBLICATIONS

Leng et al., Rapid synthesis of metal-organic frameworks MIL-101(Cr) without the addition of solvent and hydrofluoric acid, Crystal Growth & Design, Jan. 28, 2016, vol. 16, No. 3, pp. 1168-1171.

Paseta et al., Solventless synthesis of MOFs at high pressure, ACS Sustainable Chemistry & Engineering, May 30, 2016, vol. 4, No. 7, pp. 3780-3785.

Tella et al, Template metal-organic frameworks: solvent-free synthesis, characterization and powder X-ray diffraction studies of $[Cu(NO3)_2(bipy)_2](py)_2$, Journal of Porous Materials, Aug. 8, 2015, vol. 22, No. 6, pp. 1599-1605.

Zhang et al., Microwave-Assisted Solvent-Free Synthesis of Zeolitic Imidazolate Framework-67, Journal of Nanomaterials, 2016, vol. 2016, article ID 9648386, 9 pages.

Uzarevic et al., Mechanochemical and Solvent-free Assembly of Zirconium-Based Metal-organic Frameworks, Journal of Chemical Communications, Dec. 8, 2015, vol. 52, No. 10, pp. 2133-2136.

Pichon et al., Solvent-free synthesis of a microporous metal-organic framework, CrystEngComm, Feb. 6, 2006, vol. 8, pp. 211-214.

Fujii et al., Direct structure elucidation by powder X-ray diffraction of a metal-organic framework material prepared by solvent-free grinding, Journal of Chemical Communications, Sep. 17, 2010, vol. 46, pp. 7572-7574.

Zhang et al., Solvent-free Dense Energetic Metal-organic Framework (EMOF): To Improve Stability and Energetic Performance via in situ Microcalorimetry, Journal of Chemical Communications, Feb. 17, 2017, vol. 53, pp. 3034-3037.

Shekhah et al., A facile solvent-free synthesis route for the assembly of a highly $CO_2$ selective and $H_2S$ tolerant NiSIFSIX Metal-Organic Framework, Journal of Chemical Communications, Jul. 6, 2015, vol. 51, pp. 13595-13598.

He, Y., et al., Methane storage in metal-organic frameworks, Chemical Society Reviews, 2014, vol. 43, No. 16, pp. 5657-5678.

Yin, Z., et al., The concept of mixed organic ligands in metal-organic frameworks: design, tuning and functions, Dalton Transactions, 2015, vol. 44, No. 12, pp. 5258-5275.

Chen, D-M., et al., Ligand Symmetry Modulation for Designing Mixed-Ligand Metal-Organic Frameworks: Gas Sorption and Luminescence Sensing Properties, Inorganic chemistry, Aug. 5, 2016, vol. 55, No. 17, pp. 8892-8897.

Klimakow, M., et al., Mechanochemical synthesis of metal-organic frameworks: a fast and facile approach toward quantitative yields and high specific surface areas, Chemistry of Materials, 2010, vol. 22, No. 18, pp. 5216-5221.

* cited by examiner a b a

METAL ORGANIC FRAMEWORKS AND METHODS OF MAKING AND USING SAME

CROSS REFERENCE TO RELATED APPLICATIONS

This application claims priority to U.S. Provisional Application No. 62/380,646, filed on Aug. 29, 2016, the disclosure of which is hereby incorporated by reference.

BACKGROUND OF THE DISCLOSURE

Metal Organic Frameworks (MOFs) are a growing family of crystalline porous coordination polymers with high surface area and wide rich chemistry. In brief, these materials are a periodic array of metals or clusters coordinated by rigid polydentate organic ligands. The simpler ligand is terephthalic acid and the most common metals are 3d transition metals, lanthanides, zirconium and aluminum. In the last decade, the properties of these materials were exhaustively studied as they showed promising solutions to energy related problems like hydrogen storage, methane storage, active packaging, gas purification and separation, heating/cooling, and catalysis.

Among the gas storage applications, methane represents a remarkable problem to be solved. With a world reserve of methane around $10^{14}$-$10^{15}$ m$^3$ at standard temperature and pressure or STP (298 K, 1 atm), methane is a good candidate as transition fuel towards the use of hydrogen as clean fuel. As methane has a critical temperature at −82° C., it is impossible to liquefy at room temperature which is inconvenient and unviable from the economical point of view.

This is the main reason why in mobile devices, methane is used as adsorbed natural gas (ANG), where a porous material adsorbs the methane and allows storage of useful energy densities at lower pressures. In 1993, the Department of Energy of US (USDoE) defined the methane storage target at 35 bar as 150 v/v, which corresponds to 150 volumes of gas at STP per volume of container. Recently, Advanced Research Projects Agency-Energy (ARPA-E) of the US DoE pushed the goal to 315 v/v at 65 bar.

Several MOFs reported methane storage values close to US DoE target at 65 bar; UTSA-88a (248 v/v), UTSA-76 (257 v/v), PCN-14 (239 v/v), MOF-199 (267 v/v), among others. From all these MOFs, MOF-199 is relevant due to the commercially available ligand used in the synthesis.

In order to solve technological problems associated with MOFs previously known in the art, MOFs should be designed to improve methane storage and their production methods should be improved to become greener and reduce raw materials cost, production time and energy consumption. If these points are not accomplished, the problems will become bigger or remain unsolved. The production of MOFs at the laboratory scale consists of dissolving the metallic salt and the linker in an organic solvent or mix of solvents. Most of the time N,N-dimethylformamide (DMF) is used, which is difficult to recycle due to decomposition during distillation. A greener scalable method was developed by James et al.; in this case the precursor salts and the ligands are ground together with no solvent. Even if this process is green at first glance; the counter ions of the salt remain in the MOF structure, requiring the use of solvents to remove them for later applications. An electrochemical process was also reported by Müller et al. In this case, no solvent is required for removing the counter ions but the use of an energy source and disposal of exhausted electrochemical solutions should be included in the sustainability equation.

SUMMARY OF THE DISCLOSURE

In an aspect, the present disclosure provides methods of making MOFs. The methods are based on an acid-base reaction that provides MOFs. The method is flexible for making MOFs with ligand mixtures. The instant methods can be used to obtain MOFs without the need of time consuming washing steps. As the organic ligands are acids (e.g., polyfunctional organic ligands such as, for example, terephthalic acid), and the metal sources (e.g. metal hydroxide) are bases, the method can be described as an acid-base reaction. A desirable way to perform the methods of this disclosure is to perform a mixing process (e.g., a mechanical mixing such as, for example, a grinding process) of the starting materials. Before the reactants are mechanically mixed (e.g., grinded) solvent (e.g., a minimal amount of solvent) is added to enable the acid-base reaction. For example, a method of making MOFs comprises: providing a mixture of a metal source and a ligand (a starting material mixture) or mixing metal source and a ligand in the absence of a solvent to provide a starting material mixture; adding a polar solvent to the starting material mixture and mixing (e.g., mechanically mixing by, for example, grinding) the starting material mixture (e.g. reaction mixture) to which the solvent has been added, whereby MOFs are formed.

In an aspect, the present disclosure provides MOFs. The MOFs can be made using methods of the present disclosure. In an example, a MOF is made using a method of the present disclosure. The MOFs are crystalline materials, with interconnected pores in the nanometric range with one-, two- and three-dimensional periodicity of long or short range and channels and/or interconnected crystallographically defined (structural) pores. The interconnected pores in the meso and macroscale, which can be provided by the method described herein, give MOFs a porous morphology having pores that are not structural pores or crystallographically defined pores. The interconnected pores result in a MOF bulk material morphology that is distinguishable from and provides greater surface area relative to MOFs having the same or similar nominal composition (e.g., the same metal and same metal oxidation state) made by prior art methods.

The MOFs can have metals with one or more uncoordinated positions with structural ligand(s) (which can be referred to as open metal sites). Open metal sites are metal sites free of structural ligand coordination (e.g., BTC). The MOFs can have more than one class of ligand in the structure. The MOF materials with two or more ligands can have an increased number of open metal sites relative to MOF materials having only one of the ligands. The density of open metal sites can be increased, in comparison to MOFs made with one of the ligands and the same metal in the same oxidation state, by exchanging ligands.

In an aspect, the present disclosure provides uses of MOFs of the present disclosure and MOFs made using a method of the present disclosure. For example, a MOF or combination of MOFs of the present disclosure and/or a MOF or combination of MOFs made using a method of the present disclosure are used for gas (e.g., methane) storage, gas purification, and the like.

In various examples, a MOF or combination of MOFs of the present disclosure and/or a MOF or combination of MOFs made using a method of the present disclosure are used in a method of gas (e.g., methane) storage. In various examples, a MOF or combination of MOFs of the present disclosure and/or a MOF or combination of MOFs made using a method of the present disclosure are used in a method of gas purification.

In an example, a method of gas storage comprises contacting one or more MOFs of the present disclosure, which are contained in vessel, with a gas (e.g., methane) such that at least a portion of the gas is sequestered in the vessel. The MOF(s) may be in a pelletized form. The MOF material(s) can be used in gas storage methods/systems known in the art. Suitable vessels are known in the art. Suitable methods of contacting a gas with the one MOF material(s) are known in the art. The gas can be released from the vessel as desired.

BRIEF DESCRIPTION OF THE FIGURES

For a fuller understanding of the nature and objects of the disclosure, reference should be made to the following detailed description taken in conjunction with the figures provided herein.

FIG. 11a: Ln-BTC, FIG. 11b: Sm-BTC, FIG. 11c: Gd-BTC. Unreacted BTC peaks are indicated in the figure.

DETAILED DESCRIPTION OF THE DISCLOSURE

Figure 1:
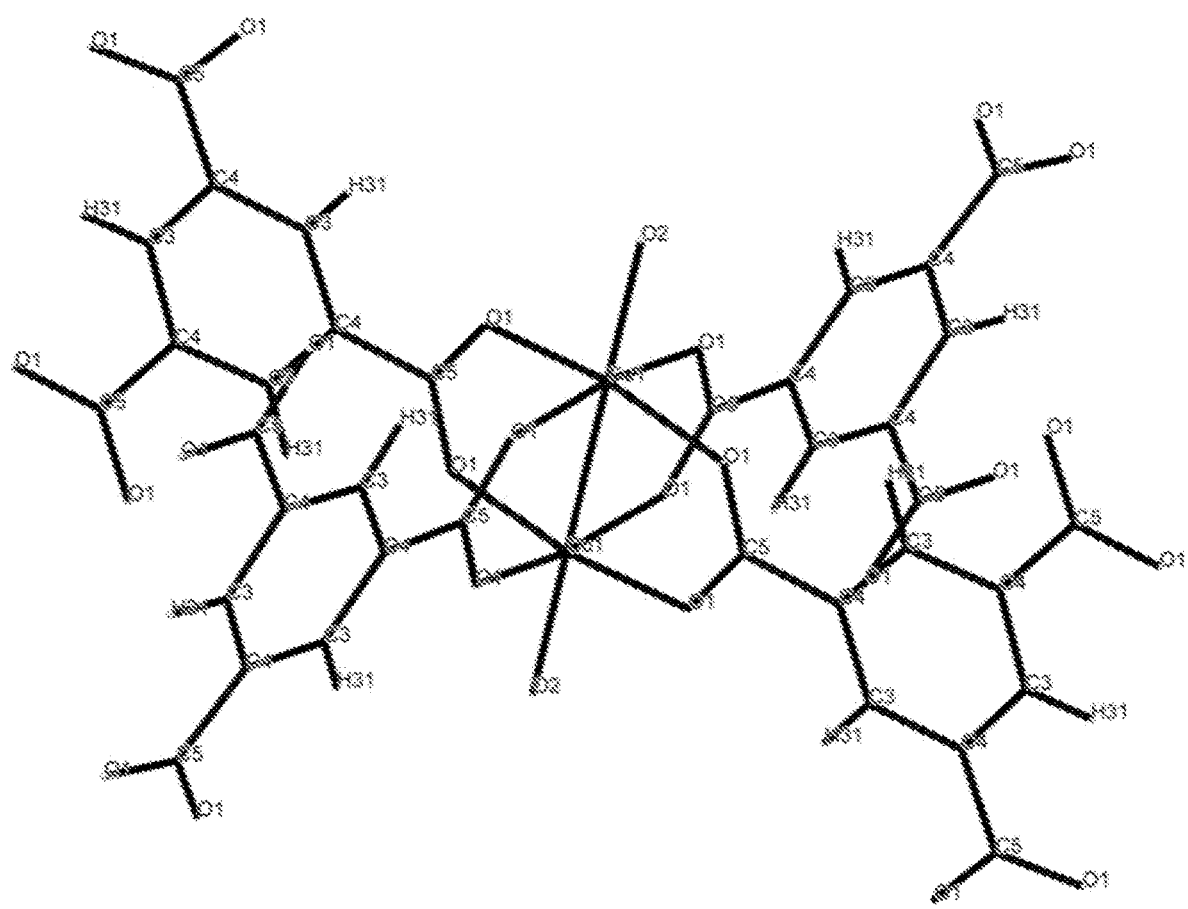
FIG. 1 shows paddlewheel in MOF-199 with a) 100% BTC ligands and b) with 75:25 BTC:iBDC substitution (BTC=trimesic acid, benzene-1,3,5-tricarboxylic acid and iBDC=isophthalic acid, benzene-1,3-dicarboxylic acid).
Figure 1:
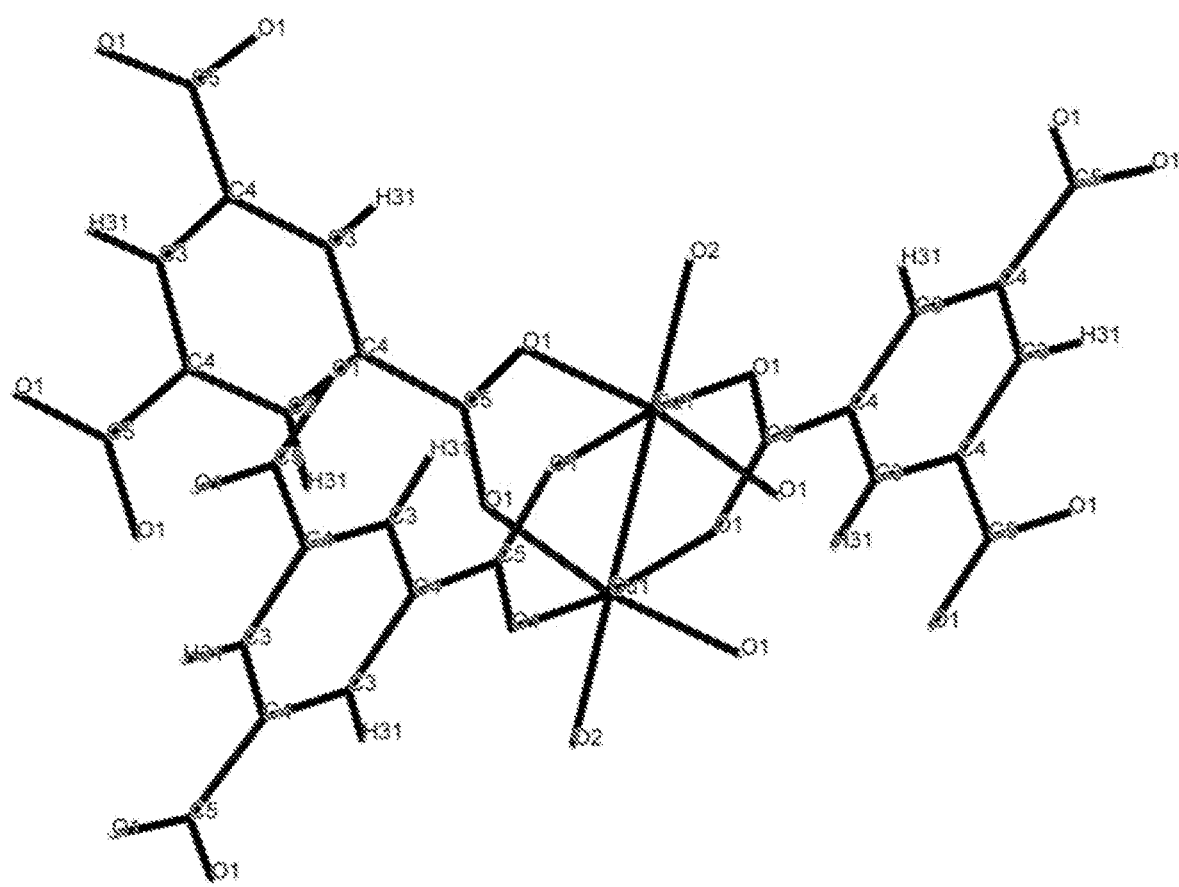

Although claimed subject matter will be described in terms of certain embodiments, other embodiments, including embodiments that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides MOF materials. The present disclosure also provides methods of making the MOF materials and uses of the MOF materials.

This disclosure provides a single-step method for the synthesis of metal-organic frameworks (MOFs). The methods require minimum solvent usage, short time of synthesis and can leave no liquid or solid residues. The methods provide flexibility to incorporate multiple organic ligands in order to obtain MOFs with different properties. The methods disclosed herein respond to the need for sustainable chemical processes that are able to obtain products with minimum usage of harmful reagents, solvents, energy and reduced waste. Unlike previous methods, the procedures described in this disclosure, do not require post synthesis washing, and furthermore, the synthesis can be obtained in less time and with higher yields compared to prior art methods. The process is also scalable to a continuous operation.

Desirable features of the present methods include, but are not limited to:

Uses a one step process which includes a simple acid/base reaction of the reagents;

Only water is obtained as by-product of the synthesis, and it can be removed easily through drying or with/by the formation of an azeotrope (e.g., with ethanol);

Faster process: for example, the synthesis process described herein can be run in 5 minutes compared with competing methods that use 24 to 30 hours;

Reaction yield can be 100%,

No counter ions remain in the products, eliminating the washing or heating up step to eliminate them. Does not generate any liquid or solid residue because the counter ion of the metal precursor is a hydroxyl, which combines with a proton from the acid to produce water;

The method uses minimum amount of a solvent (e.g., ethanol) as grinding assistant. The solvent (e.g., ethanol) does not have to be removed from the product;

The reaction has an inner driving force, no external energy is needed like in electrochemical process;

The synthesis process can be performed at room temperature;

The processes are greener than previous methods: The process described uses, at least, 10 times less solvent than competing methods. Also no harmful (e.g., toxic) solvents are needed;

The processes are less polluting: No environmentally hazardous residues are produced during the process.

Also less energy is used;

After grinding, a MOF is obtained as a paste that can be extruded in pellets or casted/molded in desired shape for specific applications;

After drying, the MOF has a nanoporous structure which would favor the matter and heat exchange making the prepared MOF by this method desirable for gas separation, storage and any other applications that have need of these properties; and More flexible: more than one different ligand can be included in the same MOF composition.

In an aspect, the present disclosure provides methods of making MOFs. The methods are based on an acid-base reaction that provides MOFs. The method is flexible for making MOFs with ligand mixtures. The instant methods can be used to obtain, for example, pure phase of MOF199 and mixed ligand MOFs with BTC and iBDC having a proportion of 0.75:0.25 without the need of time consuming washing steps.

As the organic ligands are acids, e.g. terephthalic acid, and the metal sources are bases, the method can be described as an acid-base reaction. The starting materials are a metal source (e.g. metal hydroxide) and a ligand (e.g., polyfunctional organic ligands). For example, the reactants are dry mixed together and then solvent is added to enable the acid-base reaction. A desirable way to perform the methods of this disclosure is to perform a mechanical mixing process (e.g., a grinding process) on the mixture of starting materials at room temperature. For example, the mixture is grinded for a few minutes. The product is then dried (e.g., in an oven).

The mixing of starting materials (e.g., the starting materials are metal hydroxides and organic polyfunctional ligands) can be carried out by a grinding process at room temperature. The reactants are mixed together and a solvent is added to enable the acid-base reaction. For example, the mixture is grinded for a few minutes and the product dried in an oven.

For example, a method of making MOFs comprises: providing a mixture of or mixing a metal source and a ligand (e.g. copper hydroxide and 1,3,5-benzenetricarboxylic acid) in the absence of a solvent to provide a starting material mixture; adding a polar solvent to the starting material mixture (a reaction mixture) and mixing (e.g., mechanically mixing such as, for example, grinding) the starting material mixture to which the solvent has been added, whereby MOFs are formed (e.g., a MOF paste is formed). In another example, a method of making MOFs comprises: providing a starting material mixture including (e.g., comprising) a metal source and a ligand (e.g. copper hydroxide and 1,3,5-benzenetricarboxylic acid), where the starting material mixture does not include (e.g., comprise) a solvent; adding a polar solvent to the starting material mixture (a reaction mixture) and mixing (e.g., mechanically mixing such as, for example, grinding) the starting material mixture to which the solvent has been added, whereby MOFs are formed (e.g., a MOF paste is formed).

The metal source is a metal hydroxide. The metal source can be a crystalline hydroxide of s, p, d, and f group metals of the periodic table of elements or a non-crystalline hydroxide (e.g., amorphous hydroxide) of s, p, d, and f group metals of the periodic table of elements. The metal source can also be coordination complexes with oxo, hydroxo and/or aquo ligands of s, p, d, and f group metals of the periodic table of elements. Examples of metal sources include, but are not limited to, crystalline hydroxides of alkaline earth, transition metals, lanthanides, actinides and main group metals, non-crystalline hydroxides of alkaline earth, transition metals, lanthanides, actinides and main group metals, and coordination complexes with oxo, hydroxo and/or aquo ligands and alkaline earth, transition metals, lanthanides, actinides and main group metals. In an example, the metal source is chromium (III) hydroxide, Iron (III) hydroxide, copper(II) hydroxide, zirconium hydroxide, aluminum hydroxide, lanthanum (III) hydroxide, samarium (III) hydroxide, gadolinium (III) hydroxide, and the like.

The ligands are organic molecules comprising two or more functional groups covalently bound together (e.g., oxalic acid) or individually covalent bound to one or more organic moiety. The ligands can be rigid molecules with an extended π-electron structure. The functional groups can coordinate to a metal and can comprise oxygen, nitrogen, phosphorus, sulphur, and/or carbon. Examples of functional groups include, but are not limited to, carboxylic acid, carboxylate, amines, nitriles, isonitriles, phosphates, sulphurs, and sulphates. Mixtures of organic moieties can be used. The organic moiety of a ligand can be a short chain alkyl moiety (e.g., $C_1$ to $C_3$ alkyl moiety), a short chain alkene moiety (e.g., $C_2$ to $C_4$ alkyl moiety), polyene moiety, monocyclic or polycyclic aryl moiety or monocyclic or polycyclic heteroaryl moiety. Mixtures of ligands can be used.

Example of ligands include, but are not limited to, unsaturated polycarboxylic acids (e.g., unsaturated dicarboxylic acids), branched polycarboxylic acids (e.g., branched dicarboxylic acids), bi-, tri- and tetraphenyl polycarboxylic acids, polycyclic aromatic hydrocarbons with two or more carboxylic acid groups (e.g., biphenyl dicarboxylic acids), polyheterocyclic aromatic hydrocarbons with two or more carboxylic acid groups (naphthalenic dicarboxylic acids), and the like.

Examples of ligands include, but are not limited to, aryl or heteroaryl mono, di, or tricarboxylic acids. Examples of organic molecules include, but are not limited to, benzene dicarboxylic acids (e.g., 1,3-benzenedicarboxylic acid, 1,4-benzenedicarboxylic acid) and benzene tricarboxylic acids (e.g., 1,3,5-benzenetricarboxylic acid), pyridine carboxylic acids (e.g., isonicotinic acid), and the like.

The metal source and ligand(s) are pre-mixed in the absence of solvent in various ratios. In an example, the metal source:ligand(s) ratio is a stoichiometric ratio or a substantially stoichiometric ratio. By substantially stoichiometric it is meant that the ratio of metal source and ligand(s) (e.g., the amount of ligand(s) necessary to completely fill all of the ligand sites on the metal of the metal source or the amount of ligand(s) necessary to completely fill a desired number of sites (such as, for example, to provide a desired number of defects/open sites) on the metal of the metal source) varies by 5% or less from a stoichiometric ratio. In various examples, the ratio of metal source and ligand(s) varies by 4% or less, 3% or less, 2% or less, 1% or less, 0.5% or less or 0.1% or less from a stoichiometric ratio.

The polar solvent or mixture of polar solvents is added to the starting material mixture or after the metal source and ligands are mixed. A minimum amount of solvent is used. By "minimal amount" it is meant the quantity of solvent that allows the acid-base reaction and the reactants diffuse to complete the MOF formation. Excess of solvent is occluded in the pores of the MOF. For example, there is no free solvent in the starting material mixture (e.g., reaction mixture) after reaction. After a short period of time (e.g., a few minutes) after solvent addition, the starting material mixture (e.g., reaction mixture) becomes a paste.

The polar solvent is a polar protic solvent or polar aprotic solvent. To favour the acid base reaction, a solvent is added in minimal amounts (e.g., a molar ratio $Cu(OH)_2$:EtOH 1:4) because the proton transfer in acid-base reaction is a very favoured process. For example, the solvent is ethanol. Ethanol is considered a "green" solvent.

Examples of polar protic solvents include, but are not limited to, ethanol, methanol, water, acetic acid, formic acid, other low boiling point polar protic solvents, and the like. Examples of polar aprotic solvents include but are not limited to, ethyl acetate, tetrahydrofuran, N-methylpyrrolidone, acetone, acetonitrile, dimethyl sulfoxide, dimethylformamide, and the like. Mixtures of solvents can be used.

The starting material mixture (e.g., reaction mixture) mixture can be further mixed after addition of the solvent. After addition of solvent and, optionally, further mixing, the product has high viscosity (increased relative to the starting materials) and can be described as a paste (e.g., the product does not flow).

The mixing (e.g., mechanical mixing) of the starting material mixture can be physical mixing (e.g., a physical mixing process that includes grinding). Mixing the starting material mixture to which the solvent has been added provides a MOF product (e.g., a MOF paste). This mixing can be referred to as liquid assisted grinding. For example, the mixing is carried out with a mortar and pestle, ball milling, or the like or an equivalent thereof. In another example, the mixing is not carried out with an extruder (e.g., a high-shear extruder), for example, in one synthetic step. In an example, grinding is carried out by pressing the sample between a mortar and a pestle with downward pressure and tangential shearing force that allows a size reduction of reagents and enables a better contact for a faster and more complete reaction. In contrast to the instant grinding methods, the inner pressure generated in extruders with single screw extruder may reach up to 700 bar with torsion of 16 Nm. In an example, the mixing is not carried out with an extruder (e.g., a high-shear extruder). In an example, the mixing is carried out with a low-shear or no shear grinding method.

The mixing can be carried out for a short period of time. In various examples, the individual mixing is carried out for 10 minutes or less or 5 minutes or less. The mixing can be carried out under ambient conditions. In various examples, the mixing is carried out at a pressure of 0.8 to 1.2 atm and/or a temperature of 18 to 40° C.

The MOF product (e.g., a paste) obtained from the reaction can be extruded in pellets and dried for application without any further process. In an example, a MOF product is a pellet (e.g., an extruded pellet) that is formed directly using a method described herein and/or that does not include a binder. In an example, a MOF product is a pellet (e.g., an extruded pellet) that is formed directly from a MOF product (e.g., a MOF paste) made using a method described herein with minimal (or no) thermal drying and/or minimal (or no) thermal activation of the MOF product (e.g., MOF paste). The product MOFs can be subjected to post-reaction processes. For example, the MOF product is dried (e.g., in an oven) to remove any residual solvent. For example, the MOF product (e.g., dried MOF product) can be subjected to grinding to provide a particulate product (e.g., a powder).

The methods can provide MOF materials with high yields (e.g., 100% yield) and/or without post-preparation washing methods. The yield can be determined by XRD. In various examples, a method provides a MOF material with high yield (e.g., 100% yield) and/or without post-preparation washing methods to remove by-products such as, for example, counter ions (e.g., halides, nitrates, and the like). The counter ions can be in salt form (e.g., halide salts, nitrate salts, and the like).

The method can be described as a one-step (e.g., one reaction step) process and uses lower amounts of solvent (e.g., alcohol) than previous methods. For example, the synthesis molar ratios of Cu:trimesic acid:ethanol are 3:2:13 Also, it may be desirable to avoid the use of DMF (a high boiling point solvent), which is a harmful solvent and difficult to recycle.

An example of a method to make MOF-199. A stoichiometric ratio of metal source and ligand is used, e.g., 2.9 g of $Cu(OH)_2$, the metal source, and 4.2 g of trimesic acid, the ligand, are mixed in a mortar without any solvent. After 5 minutes, 7 mL of ethanol as minimal amount of solvent is added and the mixture is mixed for another 5 minutes until the viscosity and color of the mixture change and a paste is formed. The paste is dried to eliminate solvent and grinded if necessary.

The morphology of the MOFs obtained from the present methods can be different from that obtained via solvothermal, electrochemical, or other prior art methods (e.g., for the same nominal MOF composition). For example, prior art processes provide well-shaped microcrystals, while in the method disclosed herein provides a highly porous matrix with channels in the nanometer range (e.g., 20 nm to 200 nm). These channels enhance the gas diffusion and heat exchange, increasing the performance in gas separation, purification, storage, etc.

In an example, a method does not require high boiling point solvents (e.g., dimethyl formamide (DMF)). In an example, a method does not use a metal salt (e.g., a metal salt such as for example, a metal halide, a metal nitrate, or the like).

In an aspect, the present disclosure provides MOFs. The MOFs can be made using methods of the present disclosure. In an example, a MOF is made using a method of the present disclosure.

The MOFs are crystalline materials, with interconnected pores in the nanometric range with one-, two- and three-dimensional periodicity of long or short range and channels and/or interconnected crystallographically defined (structural) pores. The interconnected pores in the meso and macroscale, which can be provided by the method described herein, give MOFs a porous morphology having pores that are not structural pores or crystallographically defined pores. The interconnected pores can have a diameter or longest dimension perpendicular to the long axis of the pore of 20 nm to 200 nm, including integer nm values and ranges therebetween. In an example, the interconnected pores have a diameter or longest dimension perpendicular to the long axis of the pore of 20 nm to 100 nm, including integer nm values and ranges therebetween. The interconnected pores result in a MOF bulk material morphology that is distinguishable from and provides greater surface area relative to MOFs having the same or similar nominal composition (e.g., the same metal and same metal oxidation state) made by prior art methods. An example of this structure type is $Cu_3BTC_2$ (referred to as CuBTC, MOF-199 or HKUST-1) that results from the reaction 1,3,5-benzenetricarboxylic acid (BTC) and $Cu(OH)_2$.

The MOFs can have metals with one or more uncoordinated positions with structural ligand(s) (which can be referred to as open metal sites). Open metal sites are metal sites free of structural ligand coordination (e.g., BTC). The MOFs can have more than one class of ligand in the structure. The MOF materials with two or more ligands can have an increased number of open metal sites relative to MOF materials having only one of the ligands. The density of open metal sites can be increased, in comparison to MOFs made with one of the ligands and the same metal in the same oxidation state, by exchanging ligands.

For example, substitution of a ligand with iBDC produces 2 open metal sites. Accordingly, a 25% iBDC replacement results in 50% more open metal sites and a 33% iBDC replacement results in 66% more metal sites.

In an example, a MOF material with at least two ligands has 5% to 66%, including all integer % values and ranges therebetween, more open metal sites than a MOF material having the same metal and same metal oxidation state and only one of the two or more ligands. In another example, a MOF material with at least two ligands has at least 5%, at least 10%, at least 25%, at least 33%, or at least 50% more open metal sites than a MOF material having the same metal and same metal oxidation state and only one of the two or more ligands.

Without intending to be bound by any particular theory, it is considered that the presence of uncoordinated open metal sites (OMS) in MOFs can increase the methane storage capacity of the MOFs (e.g., relative to MOFs differing in composition and/or structure in that they do not have open metal sites). It is considered that the increase results from enhancement of the electrostatic interaction among the uncoordinated metal ions and the slightly polarized methane molecule.

The present disclosure provides crystalline porous compounds with one-, two- and three-dimensional periodicity of long or short range and channels and/or interconnected pores in the nanometric range, also called Metal Organic Frameworks, MOFs, that can be made using methods disclosed herein. An example of this structure type is $Cu_3BTC_2$ usually named CuBTC, MOF-199 or HKUST-1 coming from the reaction 1,3,5-benzenetricarboxylic acid (BTC) and Cu $(OH)_2$.

MOF-199 is an example of Cu based MOF with open metal sites. The structural units of MOF-199 are copper dimers coordinated by four carboxylates from 1,3,5-benzenetricarboxylic acid (BTC) and two uncoordinated positions denominated open metal sites; these units are called copper paddlewheels (see FIG. 1a). The replacement of a fraction of BTC by 1,3-benzenedicarboxylic acid (iBDC) allows to generate a carboxylate vacancy in the copper paddlewheel, and consequently, increase the density open metal sites (see FIG. 1b). The formula for conventional (unmodified) MOF-199 is $Cu_3BTC_2$ and the modified MOF-199 has a $Cu_3BTC_{2-2x}iBDC_{2x}$ formula.

X ray diffraction patterns (see FIG. 2) confirmed the conservation of MOF-199 crystallographic structure when BTC was partially replaced by iBDC. No impurities were detected by XRD when the iBCD replacement is below, for example, 25% molar/molar using methods of the present disclosure. These results gave a 33% increase of open metal sites in the material (see FIGS. 3a and 3b). Even though the crystal structure is maintained, the intensity of diffraction peaks changes due to the carboxylate vacancies (see FIG. 3). The structural differences between conventional MOF-199 and the modified MOF-199 of the present disclosure can be evidenced by: i) Scanning electron microscopy, morphology of solids obtained by described method herein exhibit a porous structure while obtained via solvothermal or electrochemical methods exhibit octahedral microcrystalline morphology ii) NMR, while BTC has 3 equivalent hydrogens and only one NMR signal, iBDC has 2 equivalent hydrogens and 2 non-equivalent hydrogens, giving 3 signals, and iii) HPLC analysis of the ligand composition is expected to show that samples are different in each ligand composition.

UiO-66 is an example of a Zr based MOF. Ui)-66 has $Zr_6O_4(OH)_4$ units coordinated by terephthalates and a general formula of $Zr_6O_4(OH)_4 (BDC)_6$. When ligand defects are present, this formula can be modified to $Zr_6O_4(OH)_4 (BDC)_{6-x}$ and open metal sites density is increased. For example, UiO-66 has the following formula: $Zr_6O_4(OH)_4 (BDC)_{6-x}$, where the MOF can have up to two missing ligands, x=2. Each ligand vacancy generates 4 open metal sites (UiO-66 does not have any open metal sites in the ideal structure (e.g., x=0)).

In an example, a MOF material has ligand defects/vacancies. For example, a MOF material (e.g., a MOF material having the same metal in the same oxidation state such as, for example, UiO-66) has 5 to 35% of the ligands vacancies (e.g., iBDC). In various examples, a MOF material (e.g., a MOF material having the same metal in the same oxidation state as UiO-66 has at least 5%, at least 10%, at least 15%, at least 20%, at least 25%, or at least 33% of the ligands vacancies (e.g., iBDC).

In an example, a MOF material has two different ligands. For example, a MOF material (e.g., a MOF material having the same metal in the same oxidation state as MOF-199 or UiO-66) has 5 to 35% of the ligands (e.g., BTC) replaced with different ligands (e.g., iBDC). In various examples, a MOF material (e.g., a MOF material having the same metal in the same oxidation state as MOF-199 has at least 5%, at least 10%, at least 15%, at least 20%, at least 25%, or at least 33% of the ligands (e.g., BTC) replaced with different ligands (e.g., iBDC).

In an aspect, the present disclosure provides uses of MOFs of the present disclosure and MOFs made using a method of the present disclosure. For example, a MOF or combination of MOFs of the present disclosure and/or a MOF or combination of MOFs made using a method of the present disclosure are used for gas (e.g., methane) storage, gas purification, and the like.

In various examples, a MOF or combination of MOFs of the present disclosure and/or a MOF or combination of MOFs made using a method of the present disclosure are used in a method of gas (e.g., methane) storage. In various examples, a MOF or combination of MOFs of the present disclosure and/or a MOF or combination of MOFs made using a method of the present disclosure are used in a method of gas purification.

In an example, a method of gas storage comprises contacting one or more MOFs of the present disclosure, which are contained in vessel, with a gas (e.g., methane) such that at least a portion of the gas is sequestered in the vessel. The MOF(s) may be in a pelletized form. The MOF material(s) can be used in gas storage methods/systems known in the art. Suitable vessels are known in the art. Suitable methods of and systems for contacting a gas with the one MOF material(s) are known in the art.

The gas can be contacted with a MOF material at various pressures and/or temperatures. In an example, a MOF material is contacted with a gas at below ambient pressure and/or below ambient temperature.

Previous to adsorption of a gas, MOF(s) (e.g., pelletized MOF(s)) may be degassed under vacuum conditions (e.g., 5.10-3 mm Hg at 323 K for 12 hours), and then temperature is increased (e.g., until 453 K at a rate of 1 K/min and held for 3 hours).

The gas can be released from the vessel as desired. For example, the gas is released from the vessel by releasing the pressure of the vessel and/or increasing the temperature (e.g., up to 453K).

The steps of the methods described in the various embodiments and examples disclosed herein are sufficient to produce the MOF of the present disclosure. Thus, in an embodiment, a method consists essentially of a combination of the steps of the methods disclosed herein. In another embodiment, a method consists of such steps.

The following examples are presented to illustrate the present disclosure. They are not intended to be limiting in any matter.

Example 1

This example provides a description of a method of the present disclosure. Described is a process for production of Cu based Metal Organic Frameworks with mixed ligands and open metal sites.

A new series of modified MOF-199 with mix ligands were prepared by a novel mechanochemical method. The method comprises a simple acid/base reaction using, for example, $Cu(OH)_2$, a mix of trimesic (BTC) and isophthalic acid (iBDC) and a minimum amount of ethanol for liquid assisted grinding (LAG) as starting materials. The method is considered green due to the avoidance of harmful solvents, the solvents used in the method can be fully recovered and no post-synthetic washes are needed to remove counter ions. The new series of MOFs retained the MOF-199 crystallographic structure with a ligand replacement up to 25% of BTC by iBDC and increasing the open metal sites in copper paddlewheels. The obtained materials exhibited a novel porous nanostructure compared with previously reported methods which give microcrystalline octahedral particles. These porous nanostructures should have an active role in the kinetics of gas purification and storage.

MOF-199 is composed by copper paddlewheels (CPW) (FIG. 1a) coordinated by 1,3,5 bencentricarboxilates (BTC), a commercially available linker. The replacement of BTC by 1,3 bencendicarboxylates (isophthalates or iBDC) (FIG. 1b) was used to increase the density of immobilized OMS without modifying the MOF-199 pores structure and accessibility to OMS.

Figure 2:
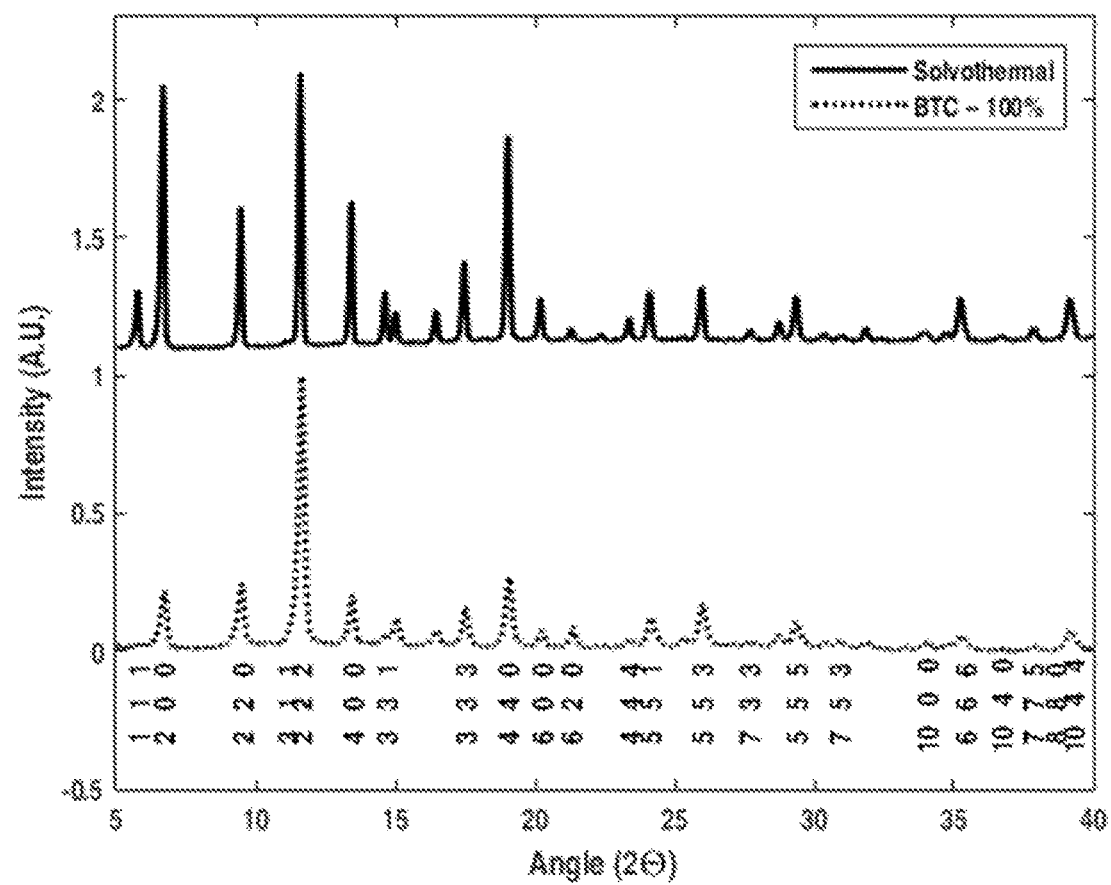
FIG. 2 shows XRD pattern of samples obtained by solvothermal and soft mechanochemical synthesis (also referred to as liquid-assisted grinding).
Figure 3:
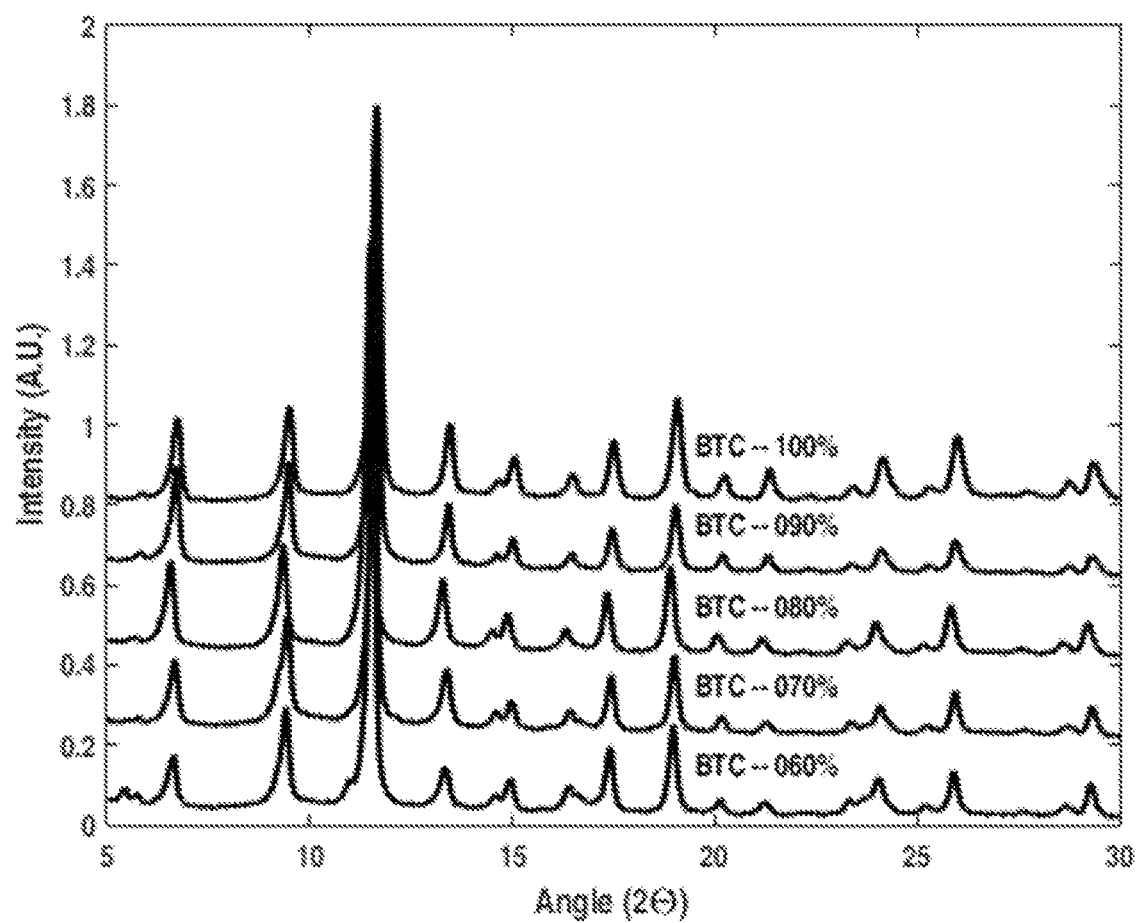
FIG. 3 shows XRD pattern of samples obtained by solvothermal and soft mechanochemical methods with different ratios of BTC:iBDC (a) and FIG. 3b—XRD pattern of samples obtained by soft mechanochemical method with increasing amount of iBDC in the range of $Cu(OH)_2$ diffraction peaks (b).
Figure 3:
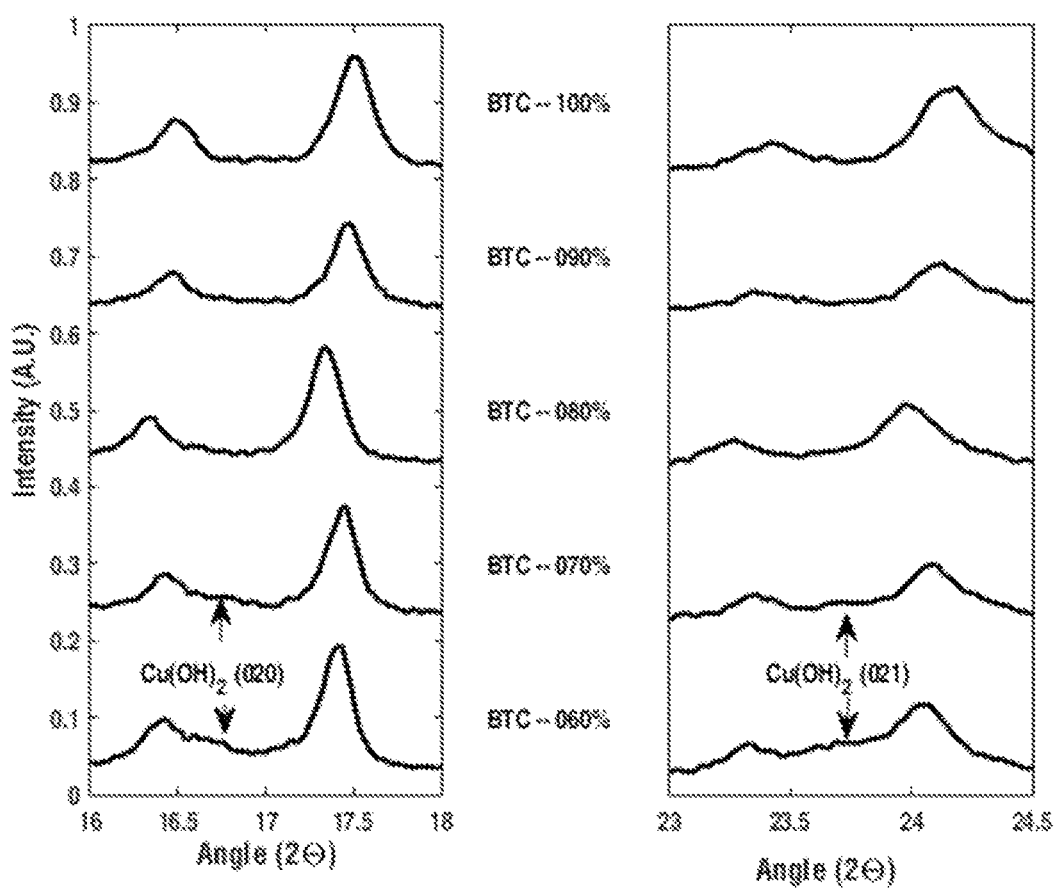

The XRD of MOF-199 samples prepared by solvotermal and mechanochemical methods are shown in FIG. 2. The peaks in both patterns correspond to a previously reported crystalline structure with no peaks corresponding to precursors of other crystalline phases. These results show that the method is an efficient approach for the synthesis of MOF-199.

The XRD patterns of mixed ligand (ML) samples are shown in FIG. 3a. All the samples showed the same pattern that MOF-199, showing the flexibility of the method to obtain MOFs with mixed ligands. The ML samples with 70 and 60% BTC shows peaks at 16.7 and 23.9 (FIG. 3b) which corresponds to unreacted $Cu(OH)_2$. Due to the impossibility to obtain Cu-iBDC with $Cu(OH)_2$ as precursor under current synthesis conditions, the limit of tolerance for ligand substitution is indicated by the appearance of the diffraction peak of $Cu(OH)_2$ instead of Cu-iBDC and in our case, this limit is placed around 20%-30% iBDC replacement.

Samples prepared by mechanochemical method show a porous nanostructure with particles around 20 nm depending on BTC:iBDC ratio. It is considered that samples with higher iBDC ratio exhibit smaller particles because iBDC ligands act as disruptions in the crystal ordering, avoiding the crystal growth and producing the smaller crystals observed. This porous nanostructure strongly differs from the MOF-199 obtained by solvothermal methods, which consists of well-defined micrometric octahedrons. The smaller particle size can be explained due to supersaturation conditions used during synthesis and porous nanostructures can be formed during solvent evaporation.

Figure 4:
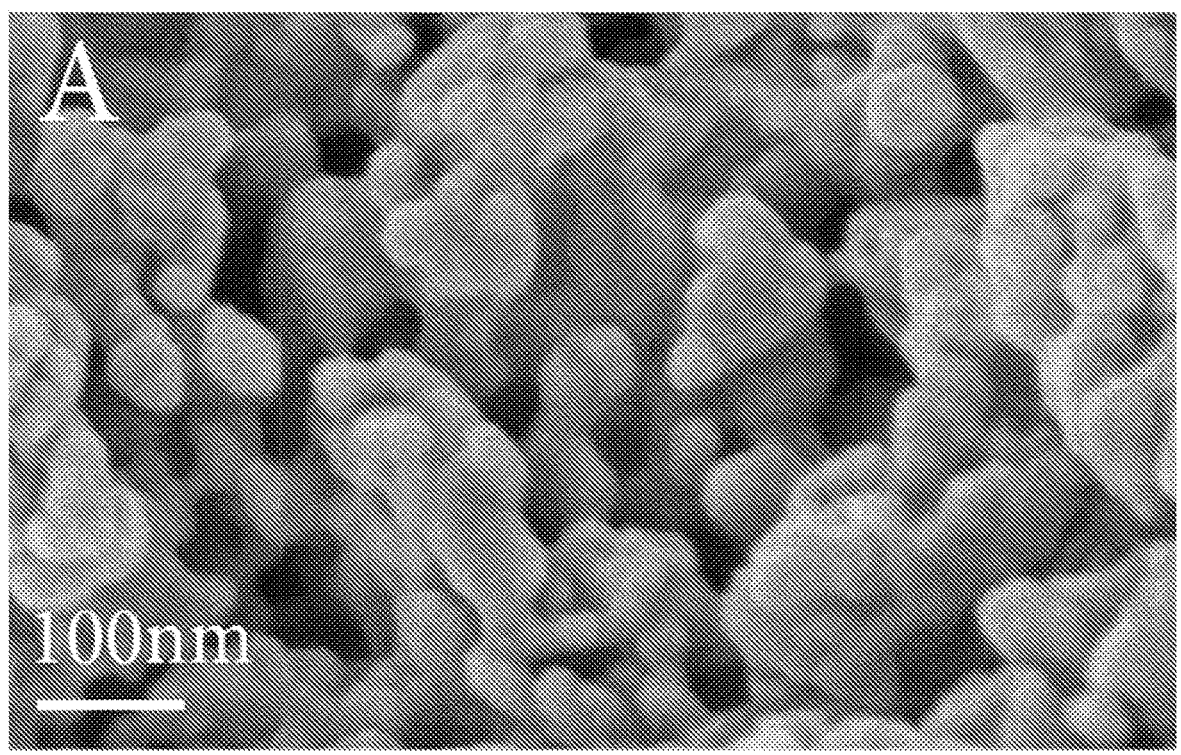
FIG. 4 shows SEM micrographs of sample prepared by mechanochemical method: a) BTC-100% and b) BTC-075%.
Figure 4:
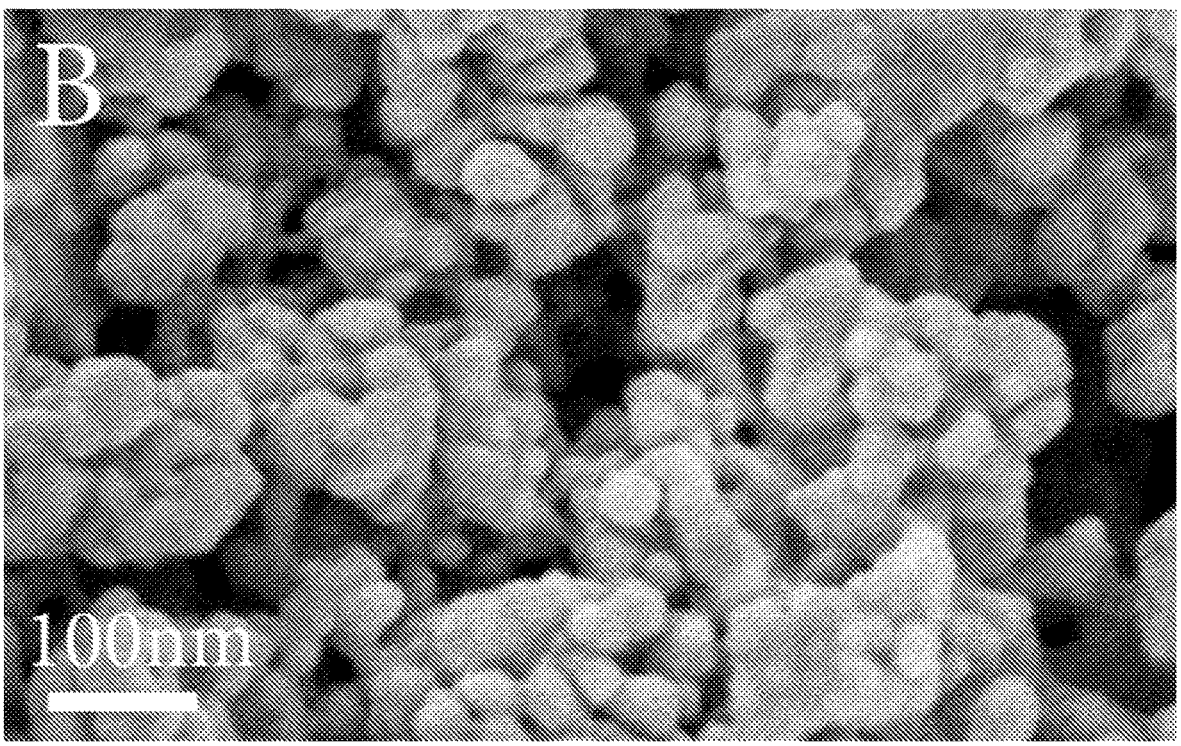

A novel method for MOFs preparation with significant advantages with respect to traditional solvothermal, slurry and electrochemical methods is presented. The use of $Cu(OH)_2$ and a mix of organic acids allowed to obtain copper-based MOFs via a simple acid-base reaction, avoiding the use of harmful solvents, with complete recovery of solvents used for liquid assisted grinding and elimination of the post-synthetic washes for counter ions removing. The flexibility of the method enabled the replacement up to 25% of BTC by iBDC under current synthesis conditions, retaining the MOF-199 structure and generating carboxylate defective copper paddlewheels which increased the density of open metal sites. The SEM micrograph exhibited a porous nanostructure unlike obtained by solvothermal or electrochemical methods (see FIGS. 4a and 4b). The combination of porous nanostructure with increased density of open metal sites makes this new series of compounds ideal for gas storage (e.g. methane).

Example 2

This example provides a description of a method of the present disclosure.

Figure 5:
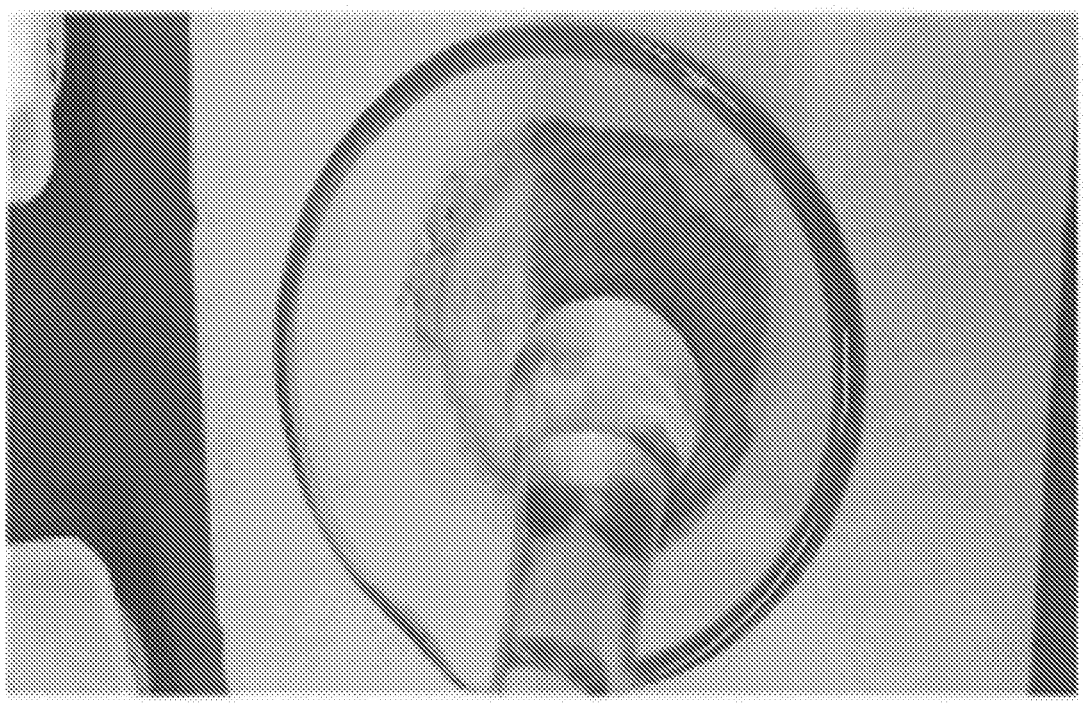
FIG. 5 shows mixing of solid reagents in a mortar. Solid reagents were mixed for 5 minutes in the mortar.
Figure 6:
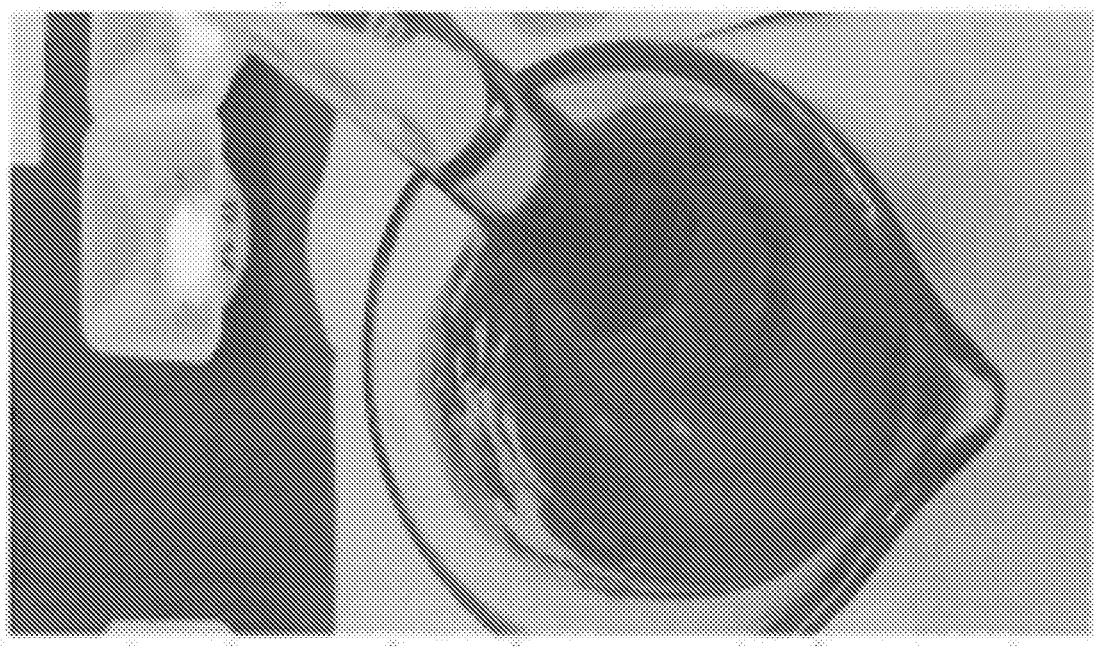
FIG. 6 is a photograph showing freshly formed MOF-199 after a few seconds of mixture between solid reagents and ethanol.
Figure 7:
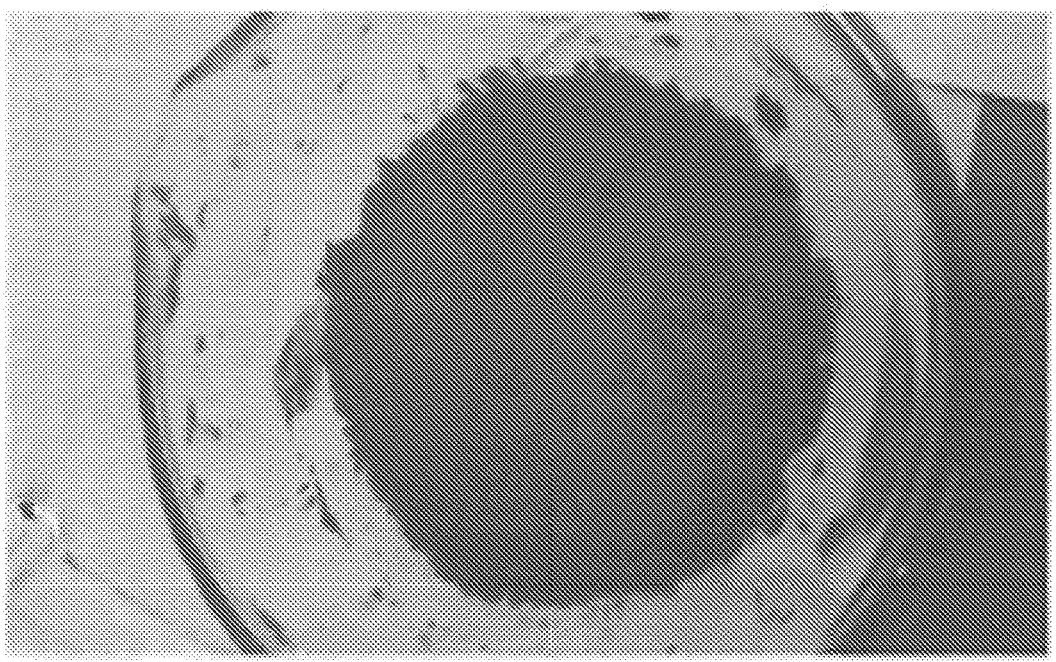
FIG. 7 is a photograph showing that after 2 minutes of continuous mixing, the solvent is completely occluded in the pores of the freshly formed MOF-199.
Figure 8:
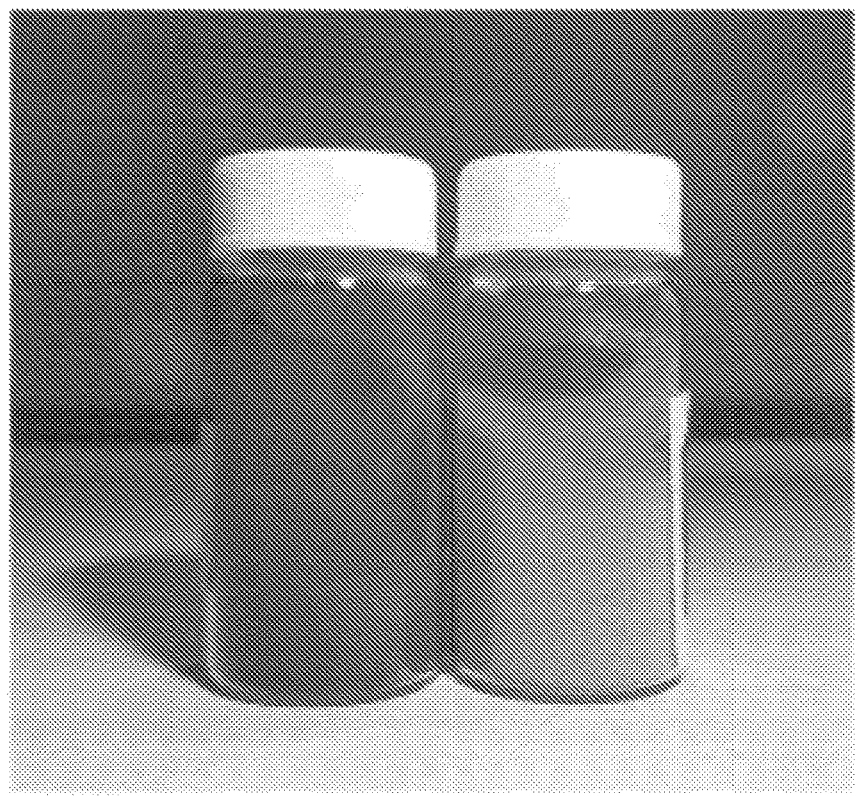
FIG. 8 is a photograph showing left sample, activated MOF-199 (after being dried in the oven) and right sample, MOF-199 dried at room temperature.

The following method was used to make MOF-199: 2.9268 g of $Cu(OH)_2$ (0.03 moles) were mixed with 4.2028 g (0.02 moles) of trimesic acid (or 1,3,5-benzentricarboxylic acid—(BTC)). 7 ml of ethanol are added to the mixture and mixed vigorously until a change in color and consistency is observed (within a minute). The complete synthesis required only 5 minutes for complete reaction of the reagents. See FIGS. 5, 6, and 7. Then, the mixture was transferred to a beaker and dried in an oven at 120° C. for 2 hours. See FIG. 8. For mixed ligand examples, molar percentages of trimesic acid were substituted with isophthalic acid (or 1,3-benzendicarboxylic acid—(iBDC)) and the same procedure was applied. No further washing or cleaning of the obtained samples was performed for characterizations.

The method can be applied to other kinds of MOFs with different ligands and metal oxides or hydroxides in the presence of ethanol or other green solvent (e.g., water).

Example 3

This example provides a description of a method of the present disclosure.

Preparation and characterization of aluminum (Al) fumarate MOFs.

Freshly precipitated Al hydroxide. 1.87 g of Al $(NO_3)_3.6H_2O$ were solubilized in 10 mL of DI water. Then, 15 mL of 10M $NH_4OH$ were added to the previous solution with vigorous agitation until a colloidal Al hydroxide was precipitated and pH value reached 7.

Al Fumarate synthesis. The freshly precipitated Al hydroxide was centrifuged and separated from the liquids. The gel was transferred to a mortar, 10 ml of absolute ethanol was added and a proper amount (stoichiometric) of fumaric acid was added. Vigorous mixing with a pestle was made for 10 minutes, and the resulting solid was transferred to an oven at 80° C. (or 120° C.) for 8 hours.

Figure 9:
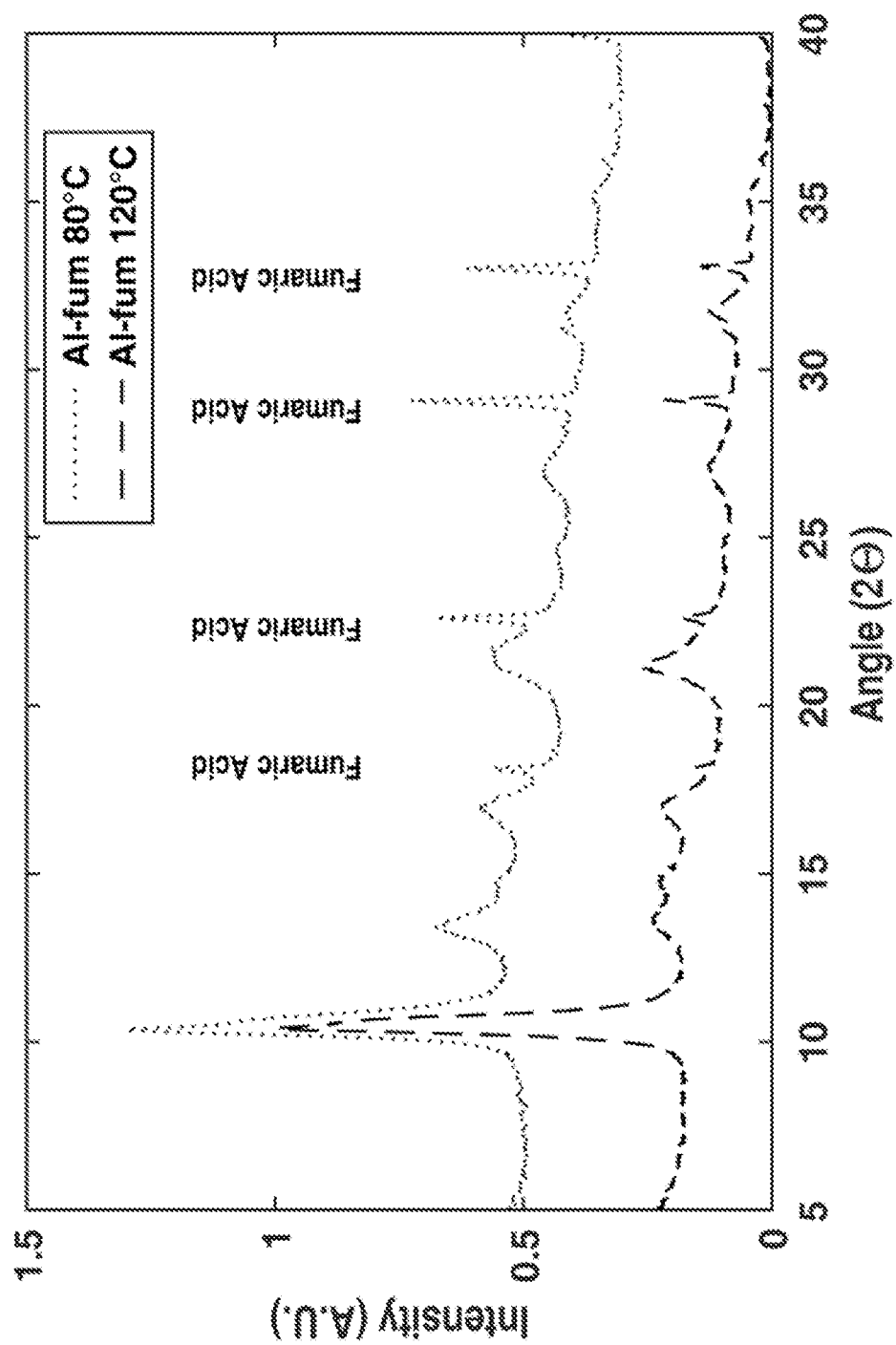
FIG. 9 shows an X ray Diffraction (XRD) pattern of as obtained Al FUM MOFs (FUM=fumaric acid, (2E)-But-2-enedioic acid) treated at two different activation/drying temperatures (80 and 120° C.). Unreacted Fumarate peaks are indicated in the figure.

Discussion XRD patterns of the two as obtained solids (Al FUM 80° C. and AL FUM 120° C.) are shown in FIG. 9. Al FUM 80° C. and Al FUM 120° C., obtained with the proposed method presented the typical XRD patterns of the reported Al FUM MOF.

Treating the as obtained solid to higher temperatures, not only consolidates the solid but also helps to complete the reaction. This can be seen in the diminution of the peak high ratio of Fumaric acid/Al FUM MOF signals around 2θ=20-25. The proposed method did not provide a 100% yield of Al FUM MOF.

Preparation and characterization of aluminum (Al) BDC MOFs.

Al BDC synthesis. To the freshly prepared Al hydroxide as described in this example, a proper (stoichiometric) amount of 1,4-benzenedicarboxylic acid (BDC) and 10 mL of absolute ethanol were added. With a mortar and a pestle, the reagents were vigorously grinded for 10 minutes. Then the as obtained solid was dried at 120° C. for 8 hours.

Figure 10:
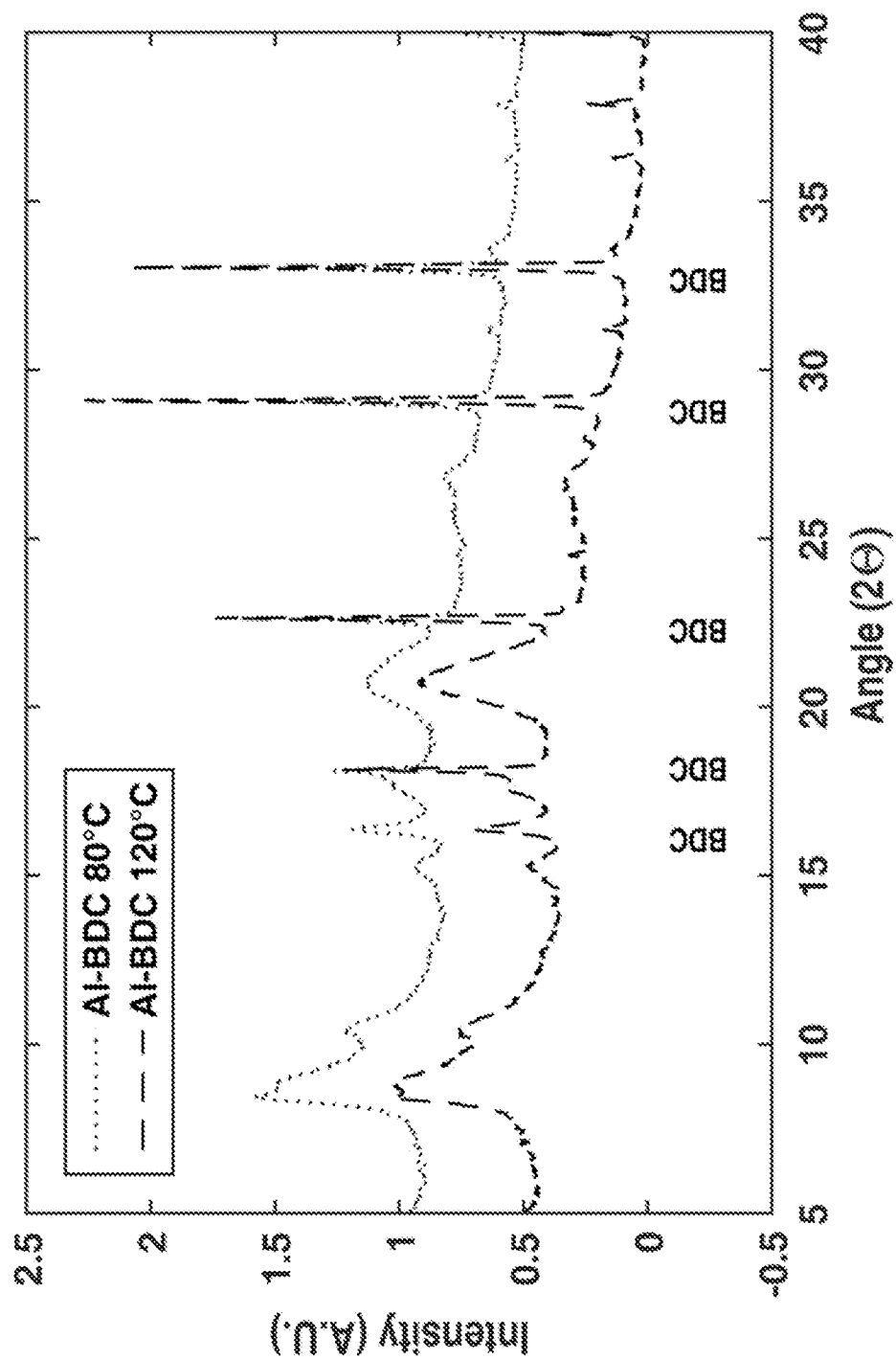
FIG. 10 shows XRD pattern of as obtained Al-BDC MOFs (BDC=Terephthalic acid, Benzene-1,4-dicarboxylic acid) treated at two different activation/drying temperatures (80 and 120° C.). Unreacted Fumarate peaks are indicated in the figure.

Discussion Typical XRD signals for Al BDC MOF were found in FIG. 10 The sample was not obtained using these conditions with 100% yield, and impurities of unreacted BDC are found.

Preparation and characterization of Lanthanide (Ln=La, Sm, Gd) MOFs.

Freshly precipitated Ln hydroxides and Ln BTC MOFs. 0.05 moles of Ln, were solubilized in 10 mL of DI. Then, 3-4 mL of $NH_4OH$ (10M) were used for obtaining the colloidal hydroxides and pH value reached was 7-8. The freshly prepared Ln hydroxide was centrifuged and separated from the liquids. Then, 0.83 g of trimesic acid (BTC) and 10 mL of absolute ethanol were added. With a mortar and a pestle, the reagents were vigorously grinded for 10 minutes. Then the as obtained solid was dried at 120° C. for 8 hours.

Figure 11:
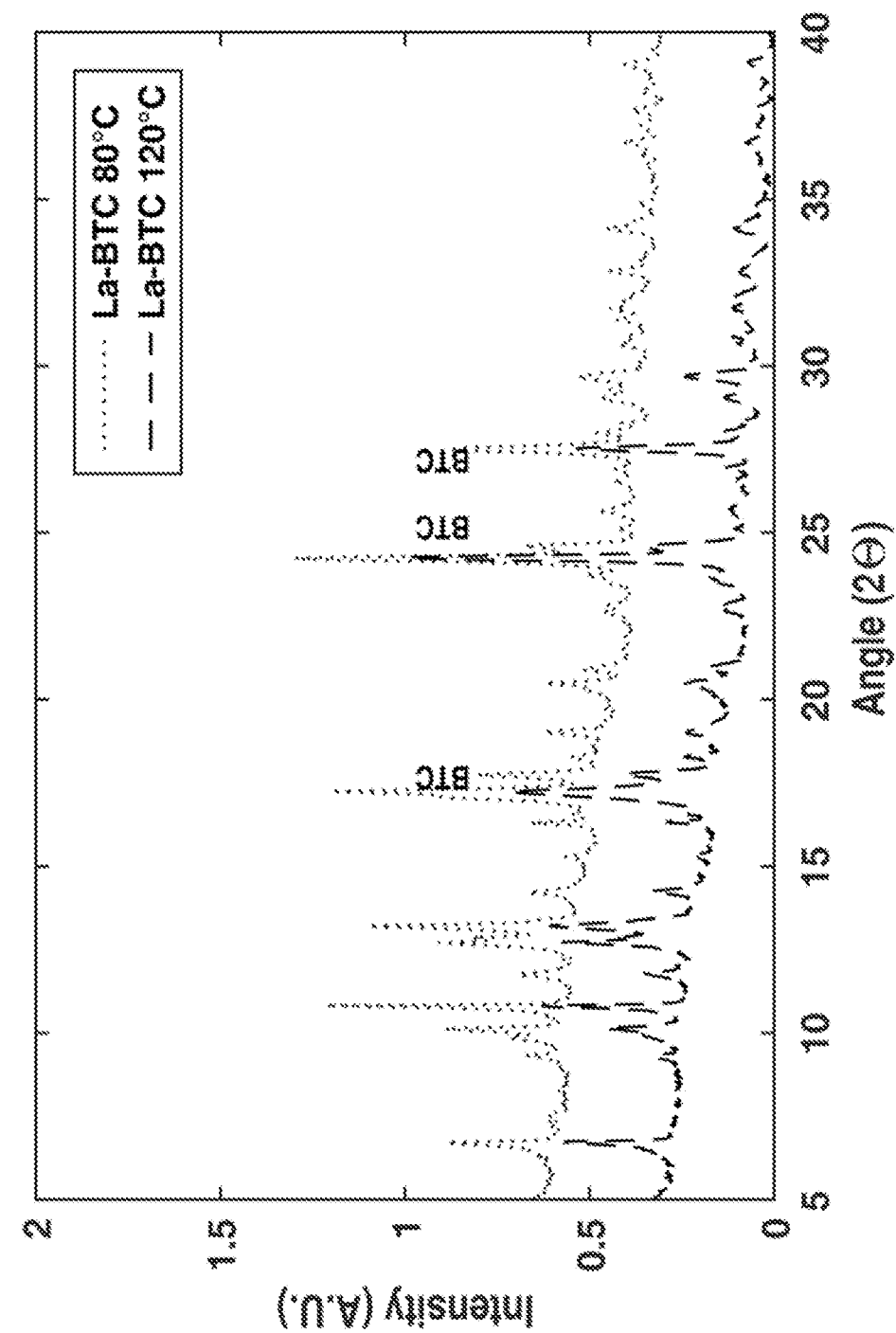
FIG. 11 shows XRD patterns of Lanthanides BTC MOFs (BTC=trimesic acid, benzene-1,3,5-tricarboxylic acid) obtained using methods of the present disclosure and treated at two different activation/drying temperatures (80 and 120° C.).
Figure 11:
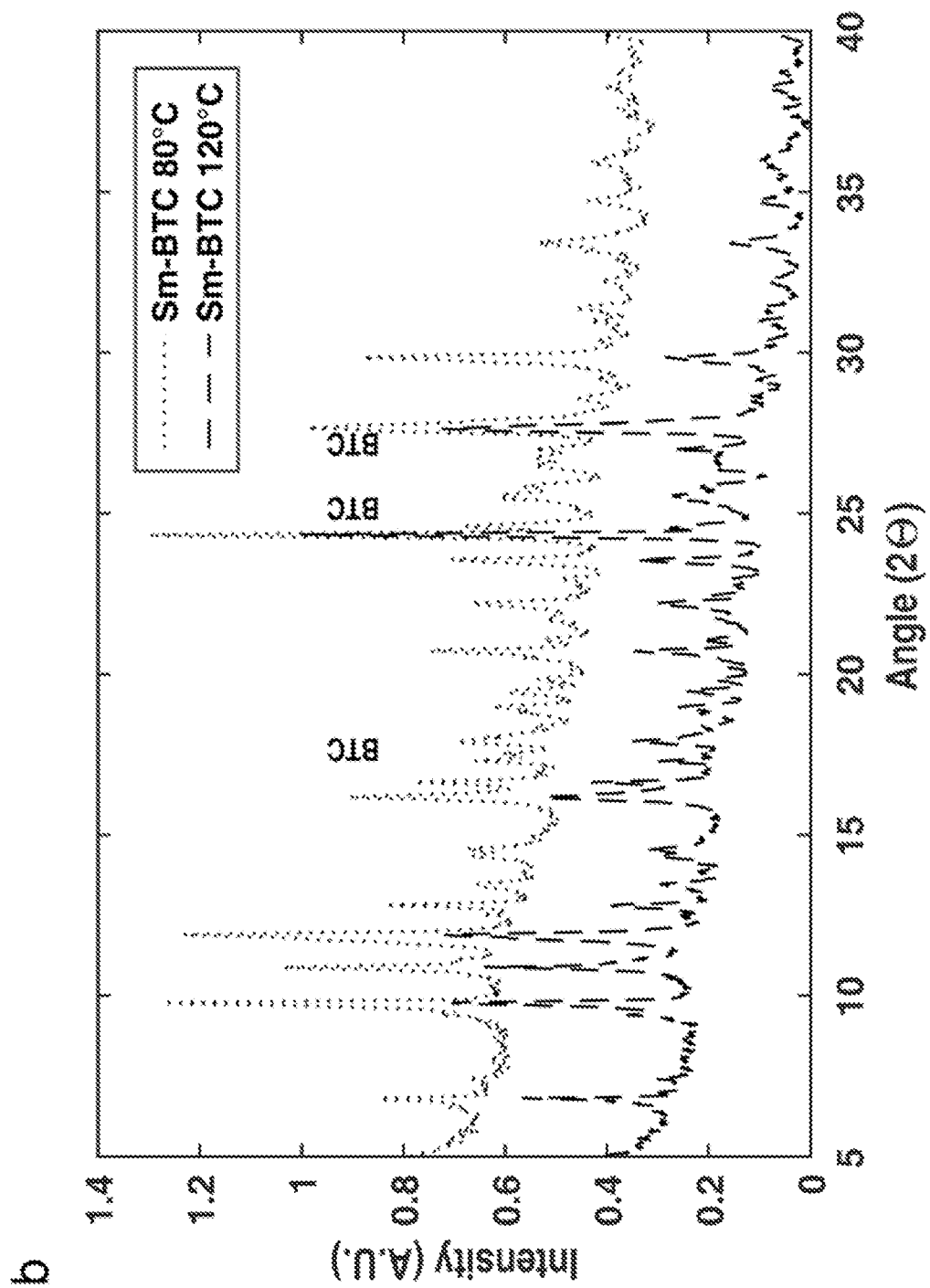
Figure 11:
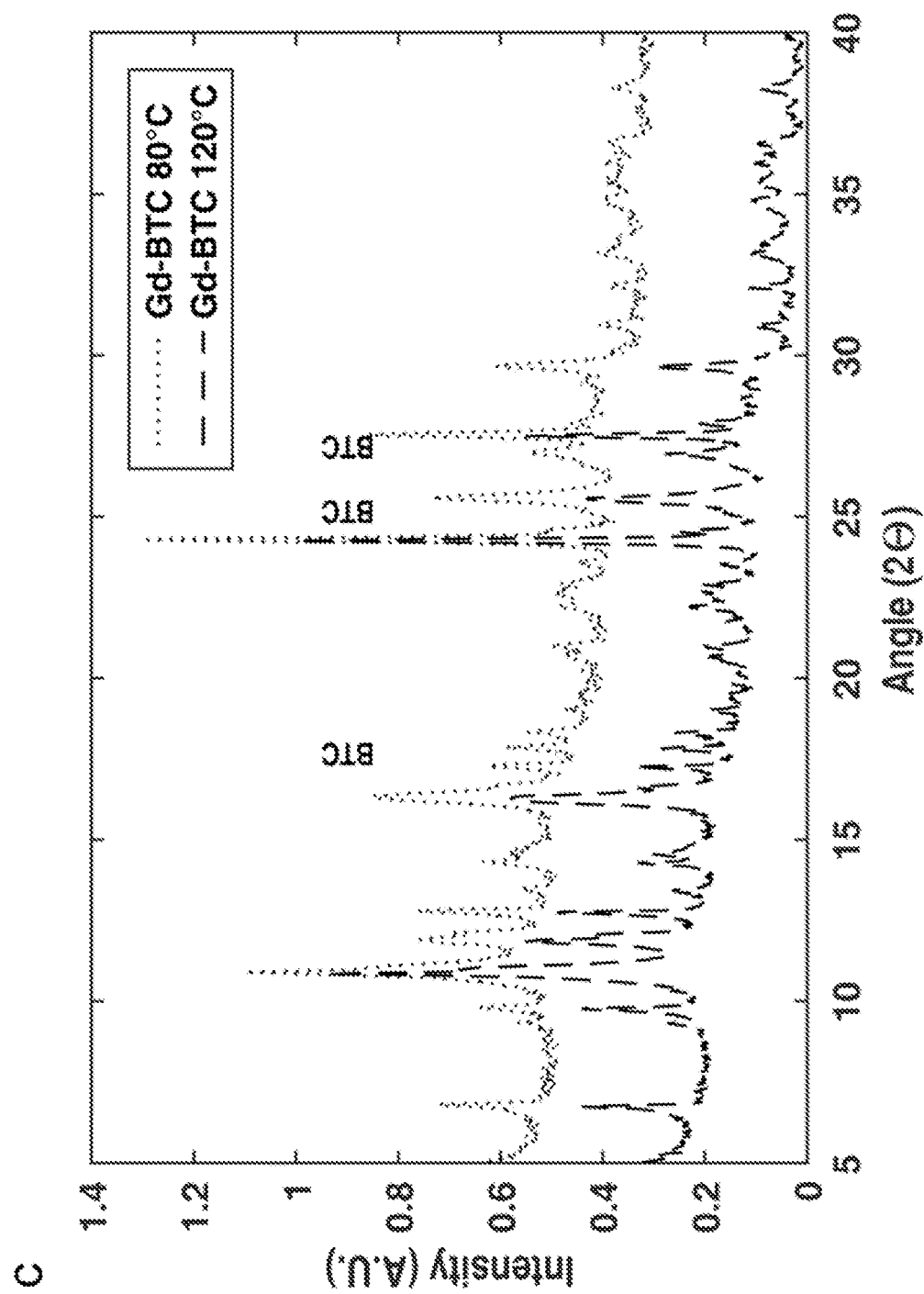

Discussion XRD peaks (FIG. 11 a, b, and c) at low angles (2θ=5-15) are typical signals of Ln=La-, Sm- and Gd-MOFs respectively. The synthesis in the present conditions did not give pure products, and remaining unreacted BTC was present.

Preparation and characterization of Cr and Fe based MOFs.

Synthesis. Freshly precipitated Cr and Fe hydroxides were obtained using 0.005 moles of $Fe(NO_3)_3.9H_2O$ and $Cr(NO_3)_3.9H_2O$ respectively. 10 mL of DI were used to solubilize the salts. Then, proper amount of $NH_4OH$ (10 m) were added to precipitate the amorphous hydroxides and reach pH=7. The precipitated was centrifuged to isolate the gels from the liquids. The freshly precipitated amorphous hydroxides were mixed in a mortar at room temperature for 10 minutes, using 10 mL of absolute ethanol as grinding assistant. Then, 0.83 g of BDC (terephthalic acid) were added and the mixture was vigorously mixed in a mortar and a pestle for 10 minutes. The obtained solids were dried in an oven at atmospheric pressure at 120° C. for 8 hours.

Figure 12:
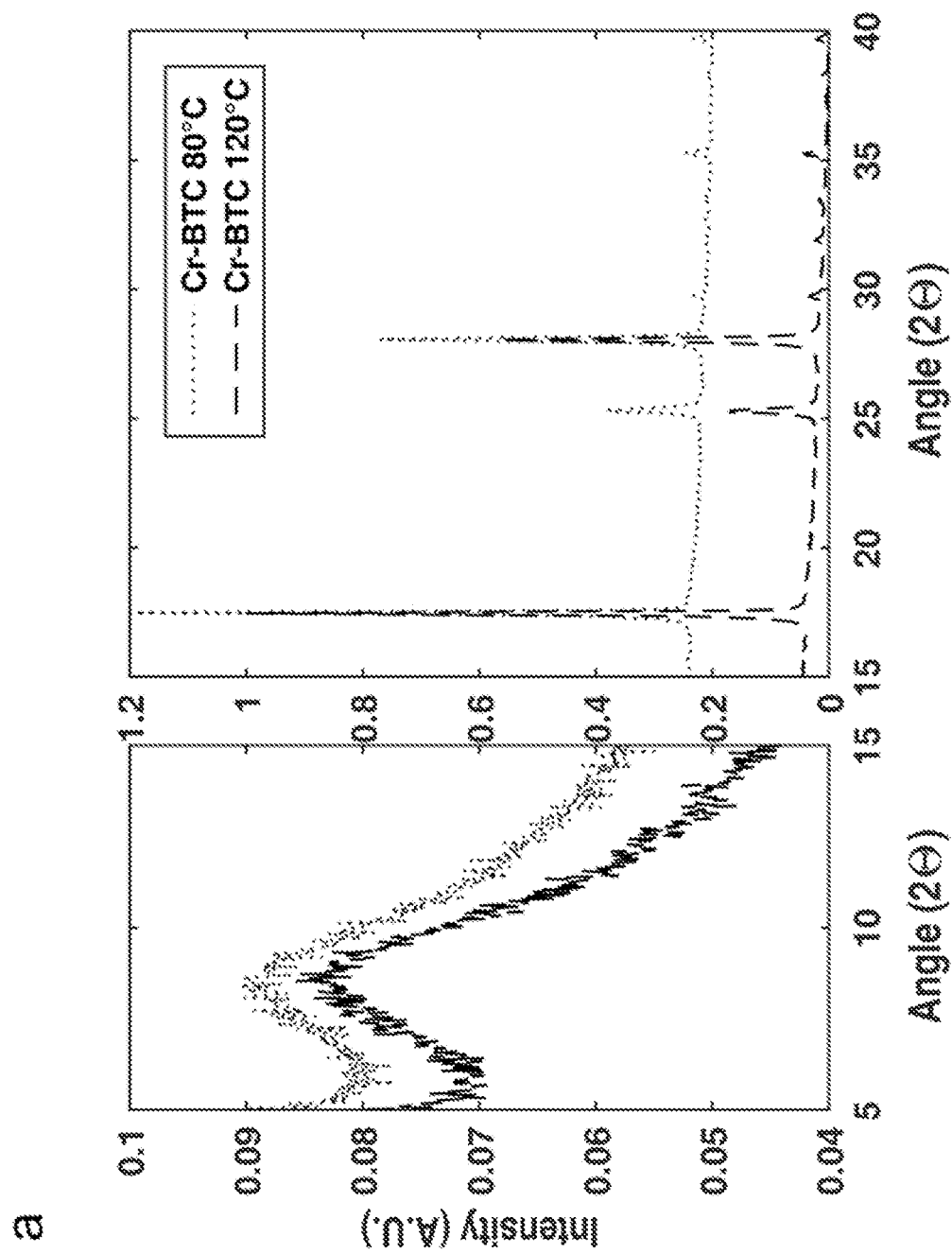
FIG. 12 shows XRD patterns of Cr-BTC (FIG. 12a) and Fe-BTC (FIG. 12b) respectively. Left side, MOFs signals. Right side, unreacted BTC signals.
Figure 12:
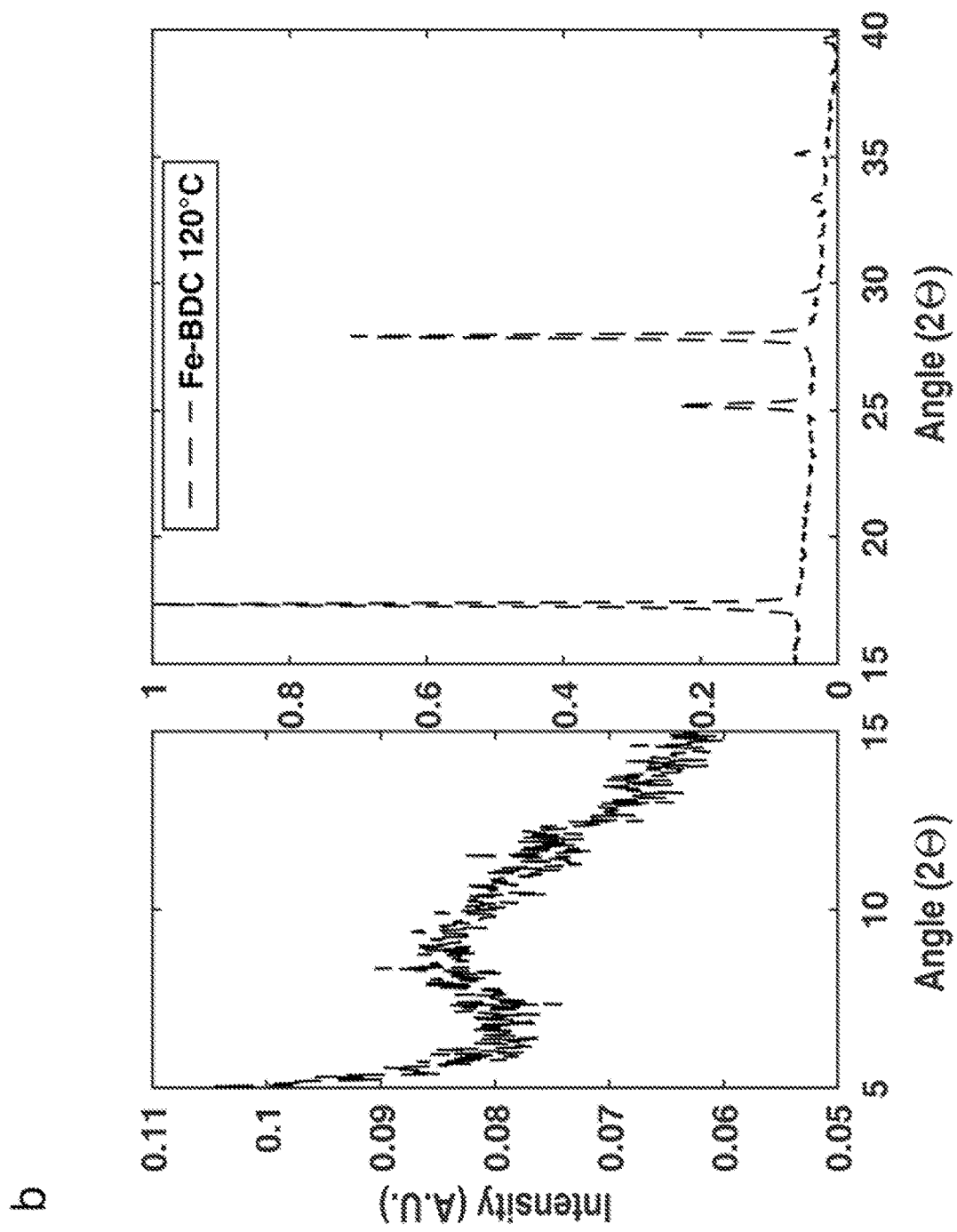
Figure 13:
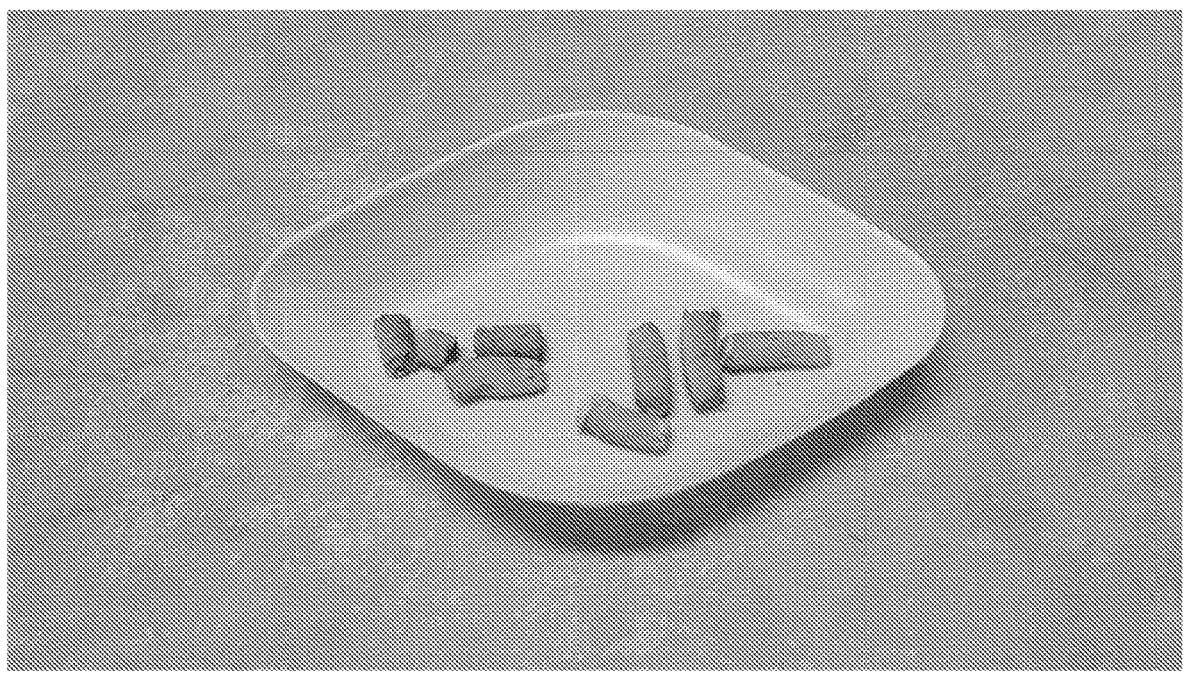
FIG. 13 shows pelletized MOF199 obtained using a method of the present disclosure.

Discussion. These MOFs are often obtained using high temperature and pressure methods, i.e., solvothermal or hydrothermal synthesis. XRD patterns of products obtained using the instant methods, gave MOF signals in XRD at low angles (2Θ below 10) shown in FIG. 12-a and b, left side, and those corresponding to trimesic acid at higher angles. (FIG. 12-a and b, right side). These methods/conditions did not provide pure phases or high reaction yield for Cr-BTC or Fe BTC MOFs.

The invention claimed is:

1. A method of making metal organic frameworks (MOFs) comprising:
providing a starting material mixture comprising: an amorphous metal hydroxide or a coordination complex with oxo, hydroxo, and/or aquo ligands of a metal; and one or more ligand that does not comprise a solvent;
adding a polar protic solvent, polar aprotic solvent, or a combination thereof to the starting material mixture, and
grinding the starting material mixture to which the polar protic solvent, polar aprotic solvent, or combination thereof has been added, whereby MOFs are formed.

2. The method of claim 1, wherein the starting material mixture comprises: the amorphous metal hydroxide or the coordination complex; and two of the ligands.

3. The method of claim 1, wherein the MOFs are dried and/or extruded to form pellets.

4. The method of claim 1, wherein the amorphous metal hydroxide is selected from the group consisting of amorphous chromium (III) hydroxide, amorphous Fe(III) hydroxide, amorphous copper(II) hydroxide, amorphous zirconium hydroxide, amorphous aluminum hydroxide, amorphous lanthanum (III) hydroxide, amorphous samarium (III) hydroxide, amorphous gadolinium (III) hydroxide, and combinations thereof, and/or wherein the metal of the coordination complex is selected from the group consisting of chromium (III), Fe(III), copper (II), zirconium (II), aluminum (III), lanthanum (III), samarium (III), gadolinium (III), and combinations thereof.

5. The method of claim 1, wherein the ligand is selected from the group consisting of unsaturated polycarboxylic acids, branched polycarboxylic acids, polycyclic aromatic hydrocarbons with two or more carboxylic acid groups, polyheterocyclic aromatic hydrocarbons with two or more carboxylic acid groups, and combinations thereof.

6. The method of claim 1, wherein the ligand is selected from the group consisting of unsaturated dicarboxylic acids, bi-, tri- and tetraphenyl polycarboxylic acids, naphthalenic dicarboxylic acids, and combinations thereof.

7. The method of claim 1, wherein the ligand is selected from the group consisting of aryl or heteroaryl mono, di, or tricarboxylic acids, and combinations thereof.

8. The method of claim 1, wherein the polar protic solvent is selected from the group consisting of ethanol, methanol, isopropanol, water, acetic acid, formic acid, and combinations thereof.

9. The method of claim 1, wherein the polar aprotic solvent is selected from the group consisting of ethyl acetate, tetrahydrofuran, N-methylpyrrolidone, acetone, acetonitrile, dimethyl sulfoxide, dimethylformamide, and combinations thereof.

10. The method of claim 1, wherein the amorphous metal hydroxide:ligand(s) ratio or the coordination complex:ligand(s) ratio is a stoichiometric ratio.

11. The method of claim 1, wherein there is no free solvent in the reaction mixture after reaction.

12. A crystalline MOF material having one or more metal ion, two or more ligands, and a porous bulk morphology comprising a plurality of interconnected pores, wherein the two or more ligands are different and the crystalline MOF material has at least 5% more open metal sites than a MOF material having the same metal(s) and the same metal oxidation state(s) and only one of the two or more ligands.

13. The crystalline MOF material of claim 12, wherein at least one of the one or more metal ion has an open metal site free of coordination with the two or more ligands.

14. The crystalline MOF material of claim 12, wherein the one or more metal ion is selected from the group consisting of chromium (III), iron (III), copper(II), zirconium(II), aluminum (III), lanthanum (III), samarium (III), gadolinium (III), and combinations thereof.

15. The crystalline MOF material of claim 12, wherein the two or more ligands are selected from the group consisting of aryl or heteroaryl mono-, di-, or tricarboxylic acids, and combinations thereof.

16. The crystalline MOF material of claim 15, wherein the two or more ligands are selected from the group consisting of benzene dicarboxylic acids, benzene tricarboxylic acids, pyridine carboxylic acids, and combinations thereof.

17. The crystalline MOF material of claim 16, wherein the two or more ligands are selected from the group consisting of 1,3-benzenedicarboxylic acid, 1,4-benzenedicarboxylic acid, 1,3,5-benzenetricarboxylic acid, isonicotinic acid, and combinations thereof.

18. The crystalline MOF material of claim 12, wherein the crystalline MOF material has 5% to 66% more open metal sites than a MOF material having the same metal(s) and the same metal oxidation state(s) and only one of the two or more ligands.

19. A method of gas storage comprising use of a MOF material of claim 12.

20. The method of claim 19, wherein the MOF material is pelletized.

21. The method of claim 1, the method further comprising preparing or precipitating the amorphous metal hydroxide or the metal coordination complex, prior to providing a starting material mixture.

22. The method of claim 1, wherein the starting material mixture comprises the amorphous metal hydroxide or the coordination complex in the form of a colloidal gel.

23. The method of claim 1, wherein the MOFs comprise two or more different ligands and have at least 5% more open metal sites than MOF materials having the same metal(s) and same metal oxidation state(s) and only one of the two or more different ligands.

24. The method of claim 1, wherein the MOFs comprise two or more different ligands and have 5% to 66% more open metal sites than MOF materials having the same metal(s) and same metal oxidation state(s) and only one of the two or more different ligands.

25. The crystalline MOF material of claim 18, wherein the pores have a diameter or longest dimension perpendicular to the long axis of the pore of 20 nm to 200 nm.

26. The crystalline MOF material of claim 12, wherein the two or more ligands consist of a first ligand and a second ligand and wherein the second ligand is 5-35% of the total ligands.

27. A method of making metal organic frameworks (MOFs) comprising:
   providing a starting material mixture comprising a metal hydroxide and two or more ligands wherein the two or more ligands are different,
   adding a polar protic solvent, polar aprotic solvent, or a combination thereof to the starting material mixture,
   grinding the starting material mixture to which the polar protic solvent, polar aprotic solvent, or combination thereof has been added, and
   forming MOFs having at least 5% more open metal sites than a MOF material having the same metal(s) and same metal oxidation state(s) and only one of the two or more ligands.

* * * * *

UNITED STATES PATENT AND TRADEMARK OFFICE
CERTIFICATE OF CORRECTION

PATENT NO. : 11,478,774 B2
APPLICATION NO. : 16/329561
DATED : October 25, 2022
INVENTOR(S) : Juan Paulo Hinestroza, Manuela Leticia Kim and Eugenio Hernan Otal Page 1 of 1

It is certified that error appears in the above-identified patent and that said Letters Patent is hereby corrected as shown below:

In the Claims

Column 16, Line 13, Claim 25, "the long" should be -- a long --.

Signed and Sealed this
Twenty-fifth Day of July, 2023

Katherine Kelly Vidal
*Director of the United States Patent and Trademark Office*